（12）United States Patent
Stromgaard et al.

(10) Patent No.: US 6,693,091 B2
(45) Date of Patent: Feb. 17, 2004

(54) **ANALOGS OF TERPENE TRILACTONES FROM *GINKGO BILOBA* FOR BIOORGANIC AND IMAGING STUDIES**

(75) Inventors: Kristian Stromgaard, New York, NY (US); Makiko Suehiro, White Plains, NY (US); Koji Nakanishi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 15 days.

(21) Appl. No.: 10/109,965

(22) Filed: Mar. 29, 2002

(65) Prior Publication Data

US 2003/0194370 A1 Oct. 16, 2003

(51) Int. Cl.[7] .......................... A61K 31/33; A61K 31/34
(52) U.S. Cl. ...................... 514/183; 514/461; 548/960; 549/297; 549/298; 424/1.81; 424/1.85; 424/1.89
(58) Field of Search ................................ 549/297, 298; 424/1.81, 1.85, 1.89; 548/960; 514/183, 461

(56) References Cited

U.S. PATENT DOCUMENTS

| | | | |
|---|---|---|---|
| 5,466,829 A | 11/1995 | Park et al. | ........... 549/297 |
| 5,541,183 A | 7/1996 | Park et al. | ........... 514/232.8 |
| 5,599,950 A | 2/1997 | Teng | ........... 549/297 |
| 6,143,725 A | 11/2000 | Vasella | ........... 514/27 |
| 6,187,314 B1 | 2/2001 | Xie et al. | ........... 424/195.1 |
| 6,221,356 B1 | 4/2001 | Junsheng | ........... 424/195.1 |

FOREIGN PATENT DOCUMENTS

| | | | |
|---|---|---|---|
| GB | 2288599 A | 10/1995 | ......... C07D/493/22 |
| WO | WO9952911 | 10/1999 | ......... C07D/493/22 |

OTHER PUBLICATIONS

Corey, E. J. & Su, W. G. (1987) *J. Am. Chem. Soc.* 109, 7534–7536. (Exhibit 9).
Corey, E. J., Kang, M. C., Desai, M. C., Ghosh, A. K., & Houpis, I. N. (1988) *J. Am. Chem. Soc.* 110, 649–651. (Exhibit 10).
Corey, E. J. & Ghosh, A. K. (1988) *Tetrahedron Lett.*. 29, 3205–3206. (Exhibit 11).
Corey, E.J. & Gavai, A.V. (1989) *Tetrahedron Lett.* 30 6959–6962. (Exhibit 12).
Corey, E.J. & Rao, K. S. (1991) *Tetrahedron Lett.* 32:4623–4626. (Exhibit 13).
Hu, L., Chen, Z., Cheng, X., & Xie, Y. (1999) *Pure Appl. Chem.* 71, 1153–1156. (Exhibit 14).
Hu, L., Chen, Z., Xie, Y., Jiang, H., & Zhen, H. (2000) *Bioorg. Med. Chem.* 8, 1515–1521. (Exhibit 15).
Hu, L., Chen, Z., Xie, Y., Jiang , Y., & Zhen, H. (2000) *J. Asian Nat. Prod. Res.* 2, 103–110. (Exhibit 16).
Hu, L., Chen, Z., & Xie, Y. (2001) *J. Asian Nat. Prod. Res.* 3, 219–227. (Exhibit 17).

*Primary Examiner*—Amelia Owens
(74) *Attorney, Agent, or Firm*—John P. White; Cooper & Dunham LLP

(57) ABSTRACT

A compound having the structure:

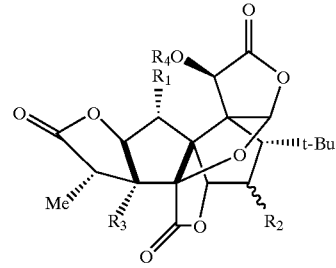

wherein $R_1$ is H, OH, a photoactivatable moiety, a fluorescent moiety, or a radioactive moiety;
   wherein $R_2$ is H, OH, a photoactivatable moiety, a fluorescent moiety, or a radioactive moiety;
   wherein $R_3$ is H or OH;
   wherein $R_4$ is H, OH, a photoactivatable moiety, a fluorescent moiety, or a radioactive moiety; and
   wherein at least one of $R_1$, $R_2$, $R_3$, or $R_4$ is a photoactivatable moiety, a fluorescent moiety, or a radioactive moiety. Optically pure enantiomers and salts of the compound are also described. Also, the synthesis of the compound, and uses of the compound, such as in a method for detecting the localization of, or identifying, receptors, enzymes or other targets, whether in a cell or in a subject.

39 Claims, 7 Drawing Sheets

WEB 2086

PAF (n = 11-13)

ANALOGS OF TERPENE TRILACTONES FROM *GINKGO BILOBA* FOR BIOORGANIC AND IMAGING STUDIES

Throughout this application, various publications may be referenced by Arabic numerals in brackets. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

*Ginkgo biloba* L., the last surviving member of a family of trees (Ginkgoacea) that appeared more than 250 million years ago, has been mentioned in the Chinese Materia Medica for more than 3,000 years (1). A number of *G. biloba* natural products have been isolated (2), the most unique being the terpene trilactones, i.e. ginkgolides A, B, C, J and M (1–5) and bilobalide (6) (FIG. 1) (3–6). The ginkgolides are diterpenes with an aesthetic cage skeleton consisting of six 5-membered rings, i.e., a spiro[4.4]nonane carbocycle, three lactones and a tetrahydrofuran. The difference between the five ginkgolides lies in the variation in the number and positions of hydroxyl groups on the spirononane framework (FIG. 1).

A standardized *G. biloba* extract (EGb 761) containing terpene trilactones (5–7%) and flavonoids (22–24%) has demonstrated neuromodulatory properties (7), and several clinical studies using EGb 761 have reported positive effects on various neurodegenerative diseases (8–13), including Alzheimer's disease (AD). In two studies involving a total of 549 AD patients, EGb 761 significantly slowed the loss of cognitive symptoms of dementia, with an efficacy in between donezepil (Aricept®) and rivastigmine (Exelon®), the two currently marketed drugs for treatment of AD symptoms (14, 15). Moreover, a recent study by Schultz and co-workers found that EGb 761 upregulated several genes in rat hippocampus and cortex, including genes expressing proteins such as transthyretin and neuronal tyrosine/threonine phosphatase, both of which are believed to be involved in AD (16). Several recent studies on healthy volunteers have shown positive effects of EGb 761 on short-term working memory (17–20) indicating that constituents of *G. biloba* also influence the brain under physiological conditions.

Although the molecular basis for the action of *G. biloba* terpene trilactone constituents on the central nervous system (CNS) is only poorly understood, it is known that the ginkgolides, particularly ginkgolide B (GB, 2), is a potent in vitro antagonist of the platelet-activating factor receptor (PAFR) (21).

PAF (1-O-alkyl-2-acetyl-sn-glycero-3-phosphocholine, FIG. 2) is a phospholipid mediator involved in numerous disorders including acute allergy, inflammation, asthma and ischemic injury. These effects are manifested through binding of PAF to the PAFR, a G protein-coupled receptor that is found in organs such as the lungs, liver, kidneys (22–24), and brain (25, 26). The function of PAF in the brain is still not clear, although PAF has been suggested to play a role in diseases of aging (27), and in initiating HIV-related neuropathogenesis (28). PAF has also been suggested as a retrograde messenger in long-term potentiation (LTP) (29, 30). However, studies using PAFR knock-out mice gave contradictory results; one study showed attenuation of LTP in the hippocampal dentate gyrus regions of mice lacking the PAFR (31), whereas another study showed that the PAFR was not required for LTP in the hippocampal CA1 region (32). These discrepancies may be due to differences in the hippocampal areas observed, as well as the assay conditions used. However, it is still unclear whether the neuromodulatory effect of the ginkgolides or the *G. biloba* extract is related to the PAFR (33, 34).

With few exceptions previous structure-activity relationship (SAR) studies of terpene trilactones on the PAFR have focused almost entirely on derivatives of GB (2). In all cases the derivatives were evaluated for their ability to prevent PAF-induced aggregation of rabbit platelets. Corey et al. investigated various intermediates encountered in the total syntheses of ginkgolide A (GA, 1) (35), GB (2) (36) and bilobalide (BB, 6) (37), and found that although the terminal methyl-bearing lactone was not essential for activity and could be replaced by other lipophilic groups (38), the tert. butyl group was important for PAFR antagonism (39). Park et al. synthesized over 200 derivatives of GB (2), with particular focus on aromatic substituents at 10-OH, and found most of them to be more potent than the parent compound (40). Similar derivatives recently synthesized by Hu et al. also yielded compounds more potent than GB (2) (41, 42), whereas other variations in GA (1) and GB (2) led to a decrease in activity (43, 44).

However, none of the cited references disclose labeled analogs of ginkgolides useful for imaging studies. The following describes the preparation of a series of ginkgolide derivatives with photoactivatable groups and fluorescent groups, as well as groups that potentially can be radiolabeled with positron emitters such as $^{11}$C or $^{18}$F. These analogs, together with the native terpene trilactones (1–6), have been assessed for their ability to displace radioligand binding to cloned PAFR.

SUMMARY OF THE INVENTION

The invention provides a compound having the structure:

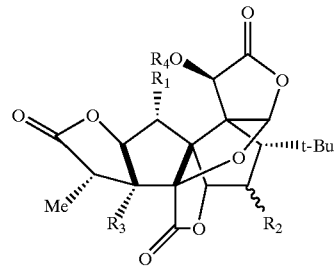

wherein $R_1$ is H, OH, a photoactivatable moiety, a fluorescent moiety, or a radioactive moiety;

wherein $R_2$ is H, OH, a photoactivatable moiety, a fluorescent moiety, or a radioactive moiety;

wherein $R_3$ is H or OH;

wherein $R_4$ is H, OH, a photoactivatable moiety, a fluorescent moiety, or a radioactive moiety; and wherein at least one of $R_1$, $R_2$, $R_3$, or $R_4$ is a photoactivatable moiety, a fluorescent moiety, or a radioactive moiety, or an optically pure enantiomer of the compound.

The invention also provides a compound having the structure:

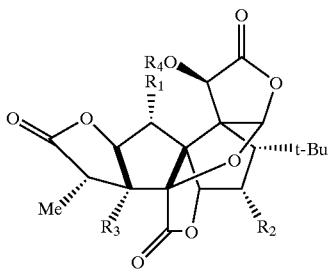

wherein $R_1$ is H, OH;

wherein $R_2$ is H, OH, F, Br, unsubstituted or substituted, straight or branched alkyl group having 1 to 5 carbon atoms, an alkenyl group having 1 to 5 carbon atoms, or a alkynyl group having 1 to 5 carbon atoms;

wherein $R_3$ is H or OH; and wherein $R_4$ is H, OH, —A—Ar, —A—Z—Ar, —$SO_2$—Ar, or —A—$NR_5$, or —$R_6$, where A is an alkylene group having 1 to 8 carbon atoms, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —$COR_5$, —$COR_6$, —$CONR_5R_6$, —$CO_2R_5$, —$NHCOR_5$, —NH(OH), —N(OH)$COR_5$, —$CHOR_5$, —$OCH_2CO_2R_5$, —$CH_2SR_5$, —$CH_2NR_5R_6$, —$SR_5$, —$OSR_5R_6$, —$NR_5R_6$, —$NR_5SO_2R_6$, in which $R_5$ and $R_6$ are the same or different and each is hydrogen, an alkyl group having 1 to 10 carbon atoms or a cycloalkyl group having 3 to 10 carbon atoms, —$SCX_3$ in which X is a halogen, —CN, —$NO_2$ or —Z—A—Z'— which Z and A are as defined above and Z' represents carbon, oxygen, sulfur, or nitrogen, or an optically pure enantiomer or a salt of the compound.

The invention also provides a compound having the structure:

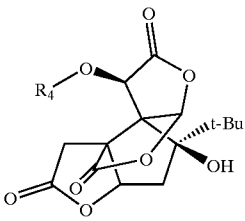

wherein $R_4$ is a photoactivatable moiety, a fluorescent moiety, or a radioactive moiety. The photoactivatable moiety, fluorescent moiety, and radioactive moiety are as defined above.

The invention also provides a compound having the structure:

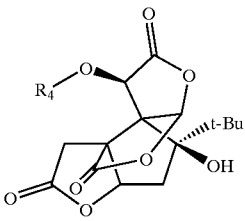

wherein $R_4$ is H, OH, —A—Ar, —A—Z—Ar, —$SO_2$—Ar, or —A—$NR_5$, or —$R_6$, where A is an alkylene group having 1 to 8 carbon atoms, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —$COR_5$, —$COR_6$, —$CONR_5R_6$, —$CO_2R_5$, —$NHCOR_5$, —NH(OH), —N(OH)$COR_5$, —$CHOR_5$, —$OCH_2CO_2R_5$, —$CH_2SR_5$, —$CH_2NR_5R_6$, —$SR_5$, —$OSR_5$, —$O_2NR_5R_6$, —$NR_5R_6$, —$NR_5SO_2R_6$, in which $R_5$ and $R_6$ are the same or different and each is hydrogen, an alkyl group having 1 to 10 carbon atoms or a cycloalkyl group having 3 to 10 carbon atoms, —$SCX_3$ in which X is a halogen, —CN, —$NO_2$ or —Z—A—Z'— in which Z and A are as defined above and Z' represents carbon, oxygen, sulfur, or nitrogen.

The invention also provides a method of detecting the localization of a receptor that binds any of the described compounds in a subject, comprising administering the compound to the subject and imaging the subject's body to identify the point of accumulation of the compound in the subject, thereby detecting the localization of the receptor in the subject.

The invention also provides a method of identifying a receptor that binds any of the described compounds in a subject, comprising administering the compound to the subject, imaging the subject's body to identify the point of accumulation of the compound in the subject, and identifying the receptor present at the point of accumulation of the compound, thereby identifying the receptor in the subject.

The terpene trilactones, ginkgolides and bilobalide, are structurally unique constituents of *Ginkgo biloba* extracts, which exhibit various neuromodulatory properties. Although the terpene trilactones are believed to be responsible for some of these effects, the specific interactions with targets in the central nervous system remain to be elucidated on a molecular level. Ginkgolides are known antagonists of the platelet-activating factor (PAF) receptor. Herein we have prepared several ginkgolide derivatives carrying photoactivatable and fluorescent groups, as wells as groups where radioactive labels can be incorporated for the purpose of performing photolabeling, ex vivo autoradiography, and positron emission tomography (PET) studies. The first examination of the binding of native terpene trilactones and their derivatives to the cloned PAF receptor is described. These studies have shown that ginkgolide derivatives with aromatic photoactivatable substituents are potent PAF receptor antagonists with $K_i$ values of 0.09–0.79 μM and hence excellent ligands for clarifying the binding of ginkgolides to PAF receptor by photolabeling studies. Ginkgolide derivatives incorporating both fluorescent and photoactivatable groups still retained binding affinity to the PAF receptor, and are promising ligands for photolabeling and sequencing. Finally, among the candidates for incorporation of radiotracers one compound was a potent antagonist of PAF receptor with a $K_i$ value of 0.99 μM and is therefore a potential ligand for probing ginkgolide-PAF receptor interactions in the brain, as well as elucidating new targets for ginkgolides.

DETAILED DESCRIPTION OF THE INVENTION

Figure 1:
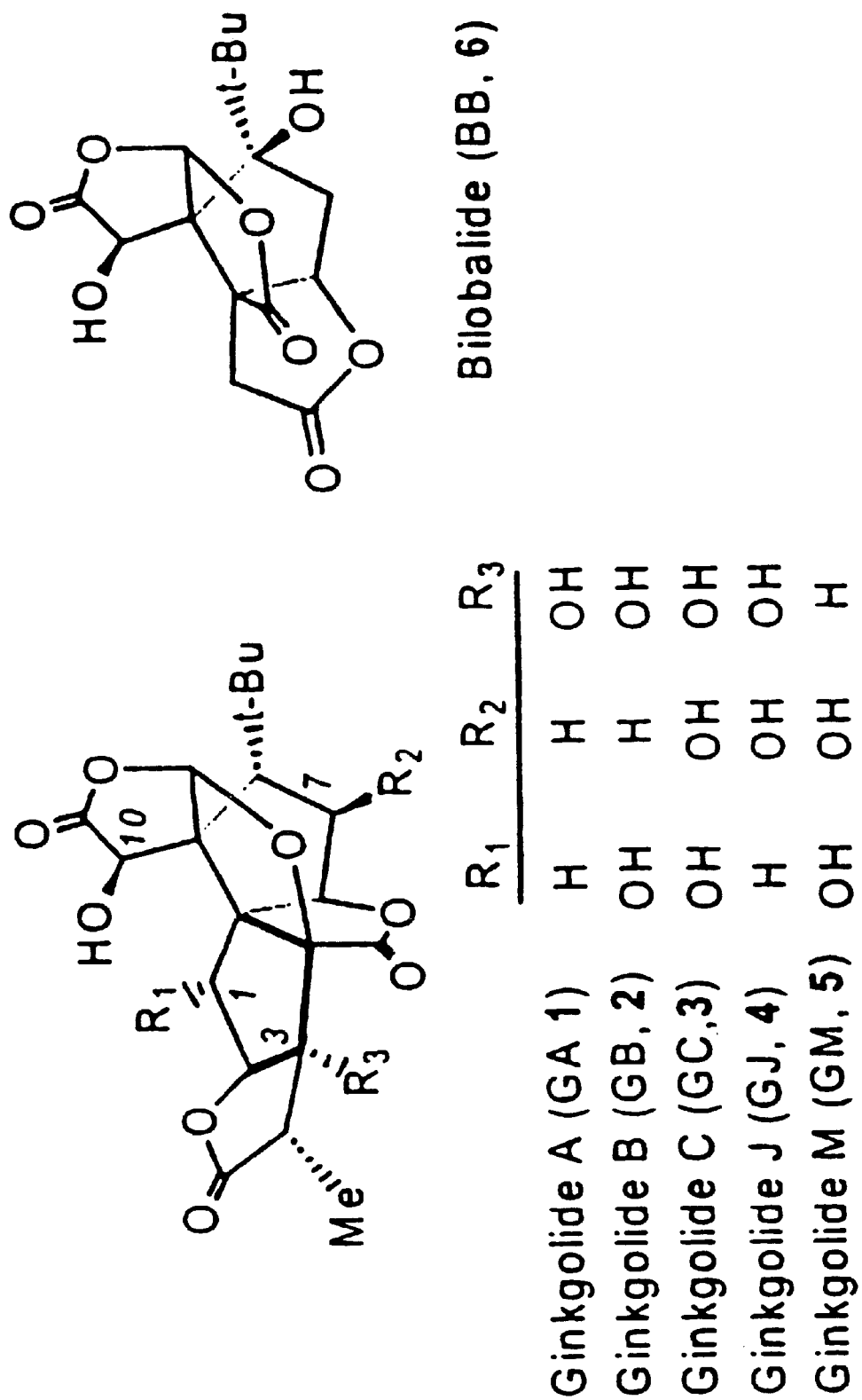
FIG. 1. Terpene trilactones isolated from *Ginkgo biloba*. GA, GB, and GC are found in the leaves and root bark of *G. biloba*, but GJ is found only in the leaves, and GM only in the root bark FIG. 2. Structures of platelet-activating factor (PAF), the endogenous ligand for the PAFR, and WEB 2086, a potent and selective antagonist, both of which have been used in radioligand binding studies.

The invention provides a compound having the structure:

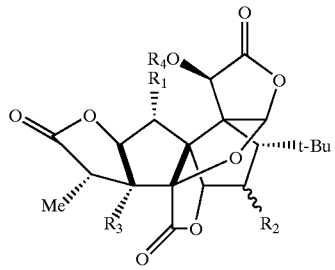

wherein $R_1$ is H, OH, a photoactivatable moiety, a fluorescent moiety, or a radioactive moiety;

wherein $R_2$ is H, OH, a photoactivatable moiety, a fluorescent moiety, or a radioactive moiety;

wherein $R_3$ is H or OH;

wherein $R_4$ is H, OH, a photoactivatable moiety, a fluorescent moiety, or a radioactive moiety; and wherein at least one of $R_1$, $R_2$, $R_3$, or $R_4$ is a photoactivatable moiety, a fluorescent moiety, or a radioactive moiety, or an optically pure enantiomer of the compound.

In the compound, $R_1$ may be a fluorescent moiety and each of $R_2$ and $R_4$ may be H or OH; $R_2$ may be a fluorescent moiety or a radioactive moiety and each of $R_1$ and $R_4$ may be H or OH; or $R_4$ may be a photoactivatable moiety or a radioactive moiety and each of $R_1$ and $R_2$ may be H or OH.

The photoactivatable moiety may be a phenylazide, a purine or pyrimidine azides, a diazoacetate, a diazoketone, a nitrobenzene, or an aryldiazonium salt. In some embodiments, the photoactivatable moiety may be benzophenone, trifluoromethyldiazirine tetrafluorophenyl, 8-azidoadenosine, 2-azidoadenosine, or 3H,3-aryldiazirine.

The fluorescent moiety may be a fluorescent amine. In some embodiments, the fluorescent moiety may be 5-(dimemethylamino)naphthalene-sulfonyl chloride, 1-(Bromoacetyl)pyrene, 3-Bromoacetyl-7-diethylaminocoumarin, 3-Bromomethyl-6,7-dimethoxycoumarin, 8-Bromomethyl-4,4-difluoro-1,3,5,7-tetramethyl-4-bora-3a,4a-diaza-s-indacene, 3-Bromomethyl-6,7-dimethoxy-1-methyl-2(1H)-quinoxazolinone, 6-Bromoacetyl-2-dimethylaminonaphthalene, or 4-(9-Anthroyloxy)phenacyl bromide.

The radioactive moiety may be $^{11}$C, $^{13}$N, $^{15}$O, $^{3}$H or $^{18}$F.

In specific embodiments of the compounds of this invention, the photoactivatable moiety may be benzophenone, trifluoromethyldiazirine or tetrafluorophenyl; the fluorescent moiety may be 5-(dimemethylamino) naphthalene-sulfonyl ("dansyl"); and the radioactive moiety may be $^{18}$F, $^{11}$C or $^{3}$H.

In a specific embodiment the invention also provides compounds having the structure:

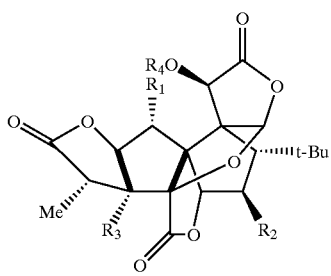

where $R_1$, $R_2$, $R_3$ and $R_4$ are defined as above.

In specific embodiments, $R_1$ may be H, OH, a fluorescent moiety; $R_2$ may be H, OH, a fluorescent moiety, or a radioactive moiety; $R_3$ may be H or OH; and $R_4$ may be H, OH, a photoactivatable moiety, or a radioactive moiety.

In yet further embodiments, $R_1$ may be —O-dansyl; or $R_2$ may be —O-dansyl; or $R_2$ may be —$^{11}CH_3$; or $R_2$ may be —$CH_2CH_2^{18}F$; or $R_2$ may be $^{18}F$; or $R_2$ may be $^3H$; or $R_4$ may be a benzophenone moiety; or $R_4$ may be a trifluoromethyldiazirine moiety; or $R_4$ may be a tetrafluorophenyl azide moiety; or $R_4$ may be —$^{11}CH_3$; or $R_4$ may be —$CH_2CH_2^{18}F$.

In one specific embodiment, the compound has the structure:

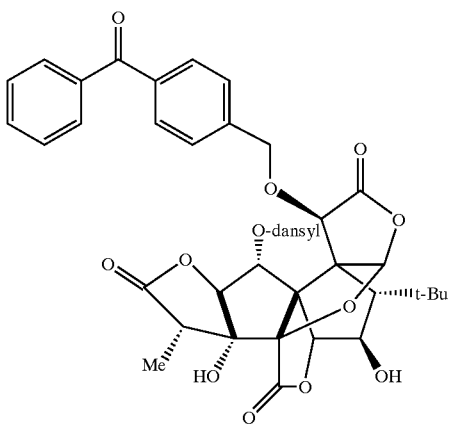

In another specific embodiment, the compound has the structure:

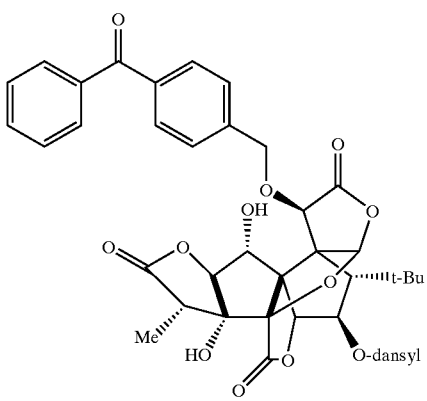

In another specific embodiment, the compound has the structure:

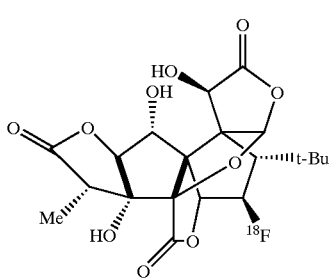

In another specific embodiment, the compound has the structure:

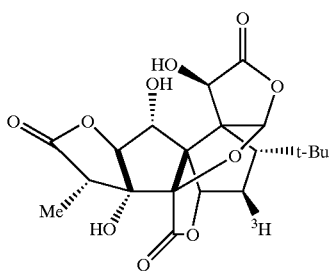

In another specific embodiment, the compound has the structure:

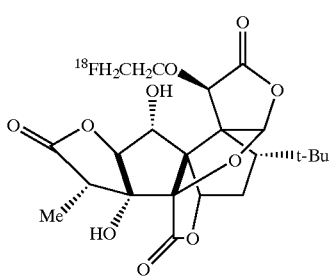

In another specific embodiment, the compound has the structure:

In another specific embodiment, the compound has the structure:

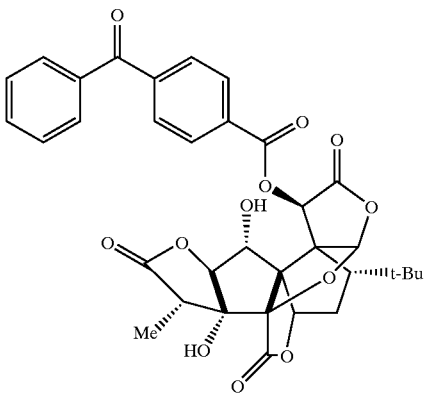

In another specific embodiment, the compound has the structure:

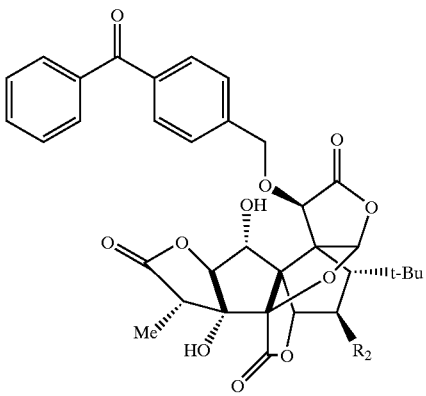

wherein $R_2$ is H or OH.

In another specific embodiment, the compound has the structure:

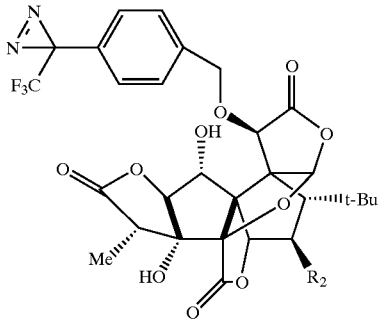

wherein $R_2$ is H or OH.

In another specific embodiment, the compound has the structure:

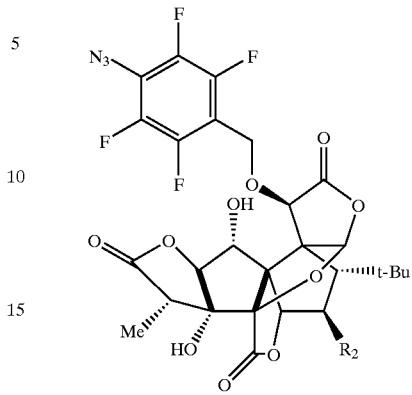

wherein $R_2$ is H or OH.

The invention also provides a compound having the structure:

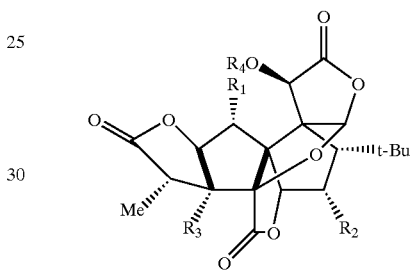

wherein $R_1$ is H, or OH;
   wherein $R_2$ is H, OH, F, Br, unsubstituted or substituted, straight or branched alkyl group having 1 to 5 carbon atoms, an alkenyl group having 1 to 5 carbon atoms, or a alkynyl group having 1 to 5 carbon atoms;
wherein $R_3$ is H or OH; and
   wherein $R_4$ is H, OH, —A—Ar, —A—Z—Ar, —SO$_2$—Ar, or —A—NR$_5$, or —R$_6$,
      where A is an alkylene group having 1 to 8 carbon atoms, which is unsubstituted or substituted by a straight or branched alkyl chain group having 1 to 5 carbon atoms;
   Z is carbon, oxygen, sulfur or nitrogen;
   Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —COR$_5$, —COR$_6$, —CONR$_5$R$_6$, —CO$_2$R$_5$, —NHCOR$_5$, —NH(OH), —N(OH)COR$_5$, —CHOR$_5$, —OCH$_2$CO$_2$R$_5$, —$CH_2SR_5$, —$CH_2NR_5R_6$, —$SR_5$, —$OSR_5$, —$O_2Nr_5R_6$, —$NR_5R_6$, —$NR_5SO_2R_6$, in which $R_5$ and $R_6$ are the same or different and each is hydrogen, an alkyl group having 1 to 10 carbon atoms or a cycloalkyl group having 3 to 10 carbon atoms, —$SCX_3$ in which X is a halogen, —CN, —$NO_2$ or —Z—A—Z'— in which Z and A are as defined above and Z' represents carbon, oxygen, sulfur, or nitrogen, or an optically pure enantiomer, or a salt of the compound.

In a specific embodiment of the above compound, $R_2$ is F.

The invention also provides a compound having the structure:

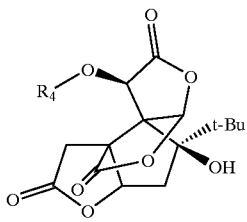

wherein $R_4$ is a photoactivatable moiety, a fluorescent moiety, or a radioactive moiety. The photoactivatable moiety, fluorescent moiety, and radioactive moiety are as defined above.

The invention also provides a compound having the structure:

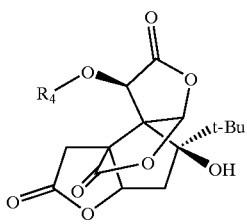

wherein $R_4$ is H, OH, —A—Ar, —A—Z—Ar, —$SO_2$—Ar, or —A—$NR_5$, or —$R_6$, where A is an alkylene group having 1 to 8 carbon atoms, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —$COR_5$, —$COR_6$, —$CONR_5R_6$, —$CO_2R_5$, —$NHCOR_5$, —NH(OH), —N(OH)$COR_5$, —$CHOR_5$, —$OCH_2CO_2R_5$, —$CH_2SR_5$, —$CH_2NR_5R_6$, —$SR_5$, —$OSR_5$, —$O_2NR_5R_6$, $NR_5R_6$, —$NR_5SO_2R_6$, in which $R_5$ and $R_6$ are the same or different and each is hydrogen, an alkyl group having 1 to 10 carbon atoms or a cycloalkyl group having 3 to 10 carbon atoms, —$SCX_3$ in which X is a halogen, —CN, —$NO_2$ or —Z—A—Z'— which Z and A are as defined above and Z' represents carbon, oxygen, sulfur, or nitrogen, or an optically pure enantiomer or a salt of the compound.

The invention also provides a process for detecting the binding of any of the described the compounds to a target, comprising contacting the compound with the target and detecting the binding of the compound to the target The target may be a DNA, enzyme or a receptor.

The invention also provides a process for detecting the localization of a receptor in a subject comprising administering any of the described compounds to the subject and detecting at any location in the subject's body to identify a point of accumulation of the compound so as to thereby localize the receptor in the subject, wherein localization of a receptor means a higher concentration of that receptor then at other points in the subject's body.

The invention also provides a process of identifying a target that binds any of the described compounds, comprising contacting the compound with the target and identifying target. The target may be a DNA, enzyme or a receptor.

The invention also provides a process of identifying a receptor that binds to any of the described compounds in a subject, comprising administering the compound to the subject, imaging the subject's body to identify the point of accumulation of the compound in the subject, and identifying the receptor present at the point of accumulation of the compound, thereby identifying the receptor in the subject.

The photoactivatable moieties react with a receptor, enzyme or other target upon irradiation and enable researchers to identify the targets of compounds, to determine the affinity and selectivity of the drug-target interaction, and to identify the binding site on the target. Examples are presented from three fundamentally different approaches: (1) photoaffinity labeling of target macromolecules; (2) photoactivation and release of "caged ligands"; and (3) photoimmobilization of ligands onto surfaces. A number of photoactivatable moieties are described in the literature, for example, aryl azides, which, when photoactivated to yield aryl nitrenes, can label any binding site containing carbon-hydrogen bonds by insertion into the C—H bond (Galardy, et al., J. Biol. Chem., 249: 350 (1974); U.S. Pat. No. 4,689,310; and U.S. Pat. No. 4,716,122); and a number of others are described in U.S. Pat. No. 6,077,698, the contents of which are hereby incorporated by reference.

The photoactivatable groups can be used for treatment as well as screening studies and diagnostics. Photoactivatable groups can be used to irreversibly bind compounds to their targets. Thus, the subject invention also provides compounds useful in methods of treatment where a desired compound is irreversibly bound to its target.

The photoactivatable groups may be phenylazides, purine and pyrimidine azides, 8-azidoadenosine, 2-azidoadenosine, diazoacetates, diazoketones, nitrobenzenes, aryldiazonium salts, or 3H,3-aryldiazirines. The preferred photoactivatable moieties for use with ginkgolides are benzophenone, trifluoromethyldiazirine and tetrafluorophenyl.

The fluorescent moiety, for example, may be 5-(dimemethylamino)naphthalene-sulfonyl chloride (dansyl chloride), a fluorescent amine such as 1-pyrenemethylamine, or any number of other groups readily available from Molecular Probes—http://www.probes.com/, the contents of which are hereby incorporated by reference. Other specific groups which are useful in this invention are 1-(Bromoacetyl)pyrene, 3-Bromoacetyl-7-diethylaminocoumarin, 3-Bromomethyl-6,7-dimethoxycoumarin, 8-Bromomethyl-4,4-difluoro-1,3,5,7-tetramethyl-4-bora-3a,4a-diaza-s-indacene, 3-Bromomethyl-6,7-dimethoxy-1-methyl-2(1H)-quinoxazolinone, 6-Bromoacetyl-2-dimethylaminonaphthalene, and 4-(9-Anthroyloxy) phenacyl bromide.

Radioactive moieties are widely known in the art and include radionuclides, radionuclides covalently attached to other groups, and metal chelates. The appropriate ginkgolide-based radioligands can be prepared using known radioactive moieties to suit the environment of use and detection method. Gamma-emitter and positron-emitter radionuclides are well-known in the art and include $^{111}$In, $^{198}$Au, $^{113}$Ag, $^{111}$Ag, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{109}$Pd, $^{105}$Rh, $^{128}$Ba, $^{197}$Hg, $^{203}$Pb, $^{212}$Pb, $^{67}$Ga, $^{68}$Ga, $^{64}$Cu, $^{67}$Cr, $^{97}$Ru, $^{75}$Br, $^{76}$Br, $^{77}$Br, $^{99m}$Tc, $^{11}$C, $^{13}$N, $^{15}$O, $^3$H and $^{18}$F. For positron emission tomography (PET) studies contemplated by this disclosure, ginkgolide derivatives labeled with the radionuclides [$^{18}$F]- and [$^{11}$C] possessing half lives of 110 min and 20 min, respectively, are preferred. While [$^3$H] is preferred for other radioactivity based studies.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Methods
Synthesis

Ginkgolides and bilobalide (1–6) were obtained as previously described (3). The syntheses of ginkgolide derivatives are outlined in FIGS. 3–7, and details appear below:

General Procedures

Anhydrous solvents were dried by eluting through alumina columns. Triethylamine was freshly distilled from NaOH pellets. Unless otherwise noted, materials were obtained from a commercial supplier and were used without further purification. All reactions were performed in pre-dried glassware under argon or nitrogen, and all reactions of involving azides or diazirines were performed in dim red light. Flash column chromatography was performed using ICN silica gel (32–63 mesh) or ICN silica gel (32–63 mesh) impregnated with sodium acetate. [van Beek, T. A. & Lelyved, G. P. (1993) Phytochem. Anal. 4, 109–114].

Thin-layer chromatography was carried out using pre-coated silica gel 60 $F_{254}$ plates with thickness of 0.25 μm. Spots were observed at 254 nm, and by staining with acetic anhydride, or cerium/molybdenum in $H_2SO_4$. $^1$H and $^{13}$C NMR spectra were obtained on Bruker DMX 300 or 400 MHZ spectrometers and are reported in parts per million (ppm) relative to internal solvent signal, with coupling constants (J) in Hertz (Hz). For $^{19}$F NMR spectra hexafluorobenzene (−162.9 ppm) was used as internal standard. High resolution mass spectra (HRMS) were measured on a JEOL JMS-HX110/100A HF mass spectrometers using a 3-nitrobenzyl alcohol (NBA) matrix and Xe ionizing gas.

EXAMPLE 1 (FIG. 3)

Synthesis of 8a–c and 9a–c—General Synthetic Procedure

GB (2) or GC (3) (0.07 mmol) was dissolved in THF (4 mL) and KH (0.008 g, 0.24 mmol) was added at room temperature. The reaction mixture was stirred for 10 min., when a solution of 7a, 7b, or 7c (0.212 mmol) in THF (1 mL) was added dropwise. The reaction was stirred at room temperature for 4 hours. The solution was then cooled to 0° C. and concentrated HCl (0.3 mL) was added. The mixture was diluted with $H_2O$ (10 mL), extracted with EtOAc (3×10 mL) and washed with sat. aq. $NH_4$Cl-solution (30 mL), brine (30 mL) and water (30 mL). The organic phase was dried ($MgSO_4$) and removed in vacuo.

Purification

The crude material is purified by flash column chromatography using either A: $CHCl_3$/MeOH (100:1 and 50:1), B: $CHCl_3$/MeOH (30:1 and 20:1), or C: cyclohexane/acetone (3:1 and 2:1) giving a white solid.

10-O-benzophenone ginkgolide B (8a)

Purified by method B. Yield: 0.035 g (78%). $^1$H NMR (400 MHZ, $CD_3OD$): δ1.13 (s, tert-butyl), 1.24 (d, J=7.1, $CH_3$), 1.92 (dd, J=14.3, 4.5, 8-H), 2.07 (td, J=13.9, 4.4, 7α-H), 2.27 (dd, J=13.5, 4.6, 7β-H), 3.06 (q, J=7.1, 14-H), 4.31 (d, J=7.2, 1-H), 4.55 (d, J=7.2, 2-H), 4.85 (d, J=11.5, benzylic-H, 1H), 5.28 (s, 10-H), 5.42 (d, J=4.0, 6-H), 5.59 (d, J=11.5, benzylic-H, 1H), 6.15 (s, 12-H), 7.53–7.60 (m, Ar—H, 4H), 7.65–7.67 (m, Ar—H, 1H), 7.77–7.82 (m, Ar—H, 4H). $^{13}$C NMR (100 MHZ, $CD_3OD$): δ7.25, 28.46 (3C), 32.18, 37.26, 42.29, 49.61, 68.21, 72.59, 72.80, 74.45, 76.76, 79.48, 83.53, 93.15, 99.78, 110.83, 127.96 (2C), 128.58 (2C), 130.03 (2C), 130.52 (2C), 132.94, 137.76 (2C), 141.67, 171.52, 172.70, 177.33, 196.45. HRMS: $C_{34}H_{34}O_{11}$ requires M+Na at m/z 641.1999, found 641.2018.

10-O-(trifluoromethyl-3H-diazirine) benzyl ginkgolide B (8b)

Purified by method B. Yield: 0.024 g (59%). $^1$H NMR (400 MHz, $CD_3OD$): δ1.11 (s, tert-butyl), 1.23 (d, J=7.1, $CH_3$), 1.89 (dd, J=14.3, 4.3, 8-H), 2.01 (td, J=13.9, 4.3, 7α-H), 2.25 (dd, J=13.4, 4.4, 7β-H), 3.05 (q, J=7.1, 14-H), 4.27 (d, J=7.3, 1-H), 4.53 (d, J=7.3, 2-H), 4.77 (d, J=11.2, benzylic-H, 1H), 5.24 (s, 10-H), 5.39 (d, J=3.9, 6-H), 5.51 (d, J=11.2, benzylic-H, 1H), 6.14 (s, 12-H), 7.29 and 7.53 (AA'BB' system, Ar—H, 4H). $^{13}$C NMR (75 MHz, $CDCl_3$): δ7.67, 21.57 (q, $^2J_{CF}$=40.9, $CCF_3$), 29.56 (3C), 32.65, 37.49, 49.31, 68.07, 72.88, 73.57, 74.57, 76.56, 77.65, 80.08, 83.90, 90.90, 99.05, 110.68, 122.33 (q, $^1J_{CF}$=274.3, $CF_3$), 127.83 (2C), 129.53 (2C), 131.06, 136.44, 171.25, 171.50, 175.87. $^{19}$F NMR (282 MHz, $CDCl_3$): δ−66.23 (s, 3F). HRMS: $C_{29}H_{29}F_3N_2O_{10}$ requires M+1 at m/z 623.1853, found 623.1834.

10-O-tetrafluorobenzylazide ginkgolide B (8c)

Purified by method B. Yield: 0.023 g (50%). $^1$H NMR (400 MHz, $CDCl_3$): δ1.13 (s, tert-butyl), 1.32 (d, J=7.0, $CH_3$), 1.84–1.97 (m, 8-H and 7α-H), 2.27–2.33 (m, 7β-H), 2.84 (d, J=3.5, 1-OH), 2.99 (s, 3-OH), 3.06 (q, J=7.0, 14-H), 4.29 (dd, J=7.9, 3.5, 1-H), 4.61 (d, J=7.9, 2-H), 4.81 (d, J=10.7, benzylic-H, 1H), 4.94 (s, 10-H), 5.39 (d, J=3.4, 6-H), 5.64 (d, J=10.7, benzylic-H, 1H), 6.03 (s, 12-H); $^{13}$C NMR (100 MHz, $CDCl_3$): δ7.70, 29.52 (3C), 32.62, 37.37, 42.03, 49.30, 61.21, 68.11, 72.79, 74.65, 80.07, 83.89, 91.00, 99.12, 108.95, 110.73, 139.71, 142.24, 144.45, 147.10, 170.69, 171.45, 175.83. $^{19}$F NMR (282 MHz, $CDCl_3$): δ−143.31 (m, 2F), −150.85 (m, 2F). HRMS: $C_{27}H_{25}F_4N_3O_{10}$ requires M+1 at m/z 628.1554, found 628.1565.

10-O-benzophenone ginkgolide C (9a)

Purified by method A. Yield: 0.023 g (64%). $^1$H NMR (400, MHz, $CD_3OD$): δ1.20 (s, tert-butyl), 1.24 (d, J=7.1, $CH_3$,), 1.78 (d, J=12.5, 8-H), 3.04 (q, J=7.1, 14-H), 4.21 (dd, J=12.5, 4.3, 7-H), 4.28 (d, J=7.0, 1-H), 4.54 (d, J=7.0, 2-H), 4.87 (d, J=11.6, benzylic-H, 1H), 5.13 (d, J=4.3, 6-H), 5.28 (s, 10-H), 5.60 (d, J=11.6, benzylic-H, 1H), 6.17 (s, 12-H) 7.53–7.61 (m, Ar—H, 4H), 7.65–7.67 (m, Ar—H, 1H), 7.77–7.83 (m, Ar—H, 4H). $^{13}$C NMR (100 MHz, CD$_3$OD): δ7.34, 28.50 (3C), 32.12, 42.26, 50.00, 64.48, 67.40, 72.77, 74.28, 75.14, 76.74, 79.49, 83.55, 93.28, 99.54, 110.63, 127.95 (2C), 128.59 (2C), 130.03 (2C), 130.53 (2C), 132.96, 137.68 (2C), 141.65, 171.41, 172.55, 177.27, 197.03. HRMS: C$_{34}$H$_{34}$O$_{12}$ requires M+1 at m/z 635.2129, found 635.2098.

10-O-(trifluoromethyl-3H-diazirine)benzyl ginkgolide C (9b)

Purified by method A. Yield: 0.023 g (51%). $^1$H NMR (400 MHz, CD$_3$OD): δ1.17 (s, tert-butyl), 1.24 (d, J=7.1, CH$_3$,), 1.76 (d, J=12.5, 8-H), 3.02 (q, J=7.1, 14-H), 4.15 (dd, J=12.5, 4.3, 7-H) 4.24 (d, J=7.0, 1-H), 4.52 (d, J=7.0, 2-H), 4.79 (d, J=11.3, benzylic-H, 1H), 5.10 (d, J=4.3, 6-H), 5.23 (s, 10-H), 5.52 (d, J=11.3, benzylic-H, 1H), 6.15 (s, 12-H), 7.29 and 7.54 (AA'BB' system, aromatic-H, 4H). $^{13}$C NMR (75 MHz, CDCl$_3$): δ7.65, 23.77 (q $^2$J$_{CF}$=38.9, CCF$_3$), 29.52 (3C), 32.65, 41.94, 50.92, 64.43, 67.48, 73.89, 74.30, 76.03, 76.34, 79.63, 83.90, 90.91, 98.94, 110.53, 122.32 (q, $^1$J$_{CF}$= 275.0, CF$_3$), 127.94 (2C), 129.68 (2C), 131.26, 136.07, 170.97, 171.07, 175.69. $^{19}$F NMR (282 MHz, CDCl$_3$): δ−66.23 (s, 3F). HRMS: C$_{29}$H$_{29}$F$_3$N$_2$O$_{11}$ requires M+1 at m/z 639.1802, found 639.1790.

10-O-tetrafluorobenzylazide ginkgolide C (9c)

Purified by method C. Yield: 0.080 g (54%). $^1$H NMR (400 MHz, CDCl$_3$): δ1.22 (s, tert-butyl), 1.33 (d, J=7.0, CH$_3$,), 1.71 (d, J=12.4, 8-H), 2.33 (d, J=10.6, 7-OH), 2.88 (d, J=3.4, 1-OH), 3.01 (s, 3-OH), 3.08 (q, J=7.0, 14-H), 4.08 (m, 7-H) 4.27 (dd, J=7.8, 3.4, 1-H), 4.62 (d, J=7.8, 2-H), 4.83 (d, J=10.7, benzylic-H, 1H), 4.96 (s, 10-H), 5.09 (d, J=4.4, 6-H), 5.58 (d, J=10.7, benzylic-H, 1H), 6.04 (s, 12-H). $^{13}$C NMR (75 MHz, CDCl$_3$): δ7.64, 29.42 (3C), 32.59, 42.08, 50.64, 51.16, 61.47, 64.35, 67.32, 74.27, 75.88, 79.64, 83.88, 91.26, 99.14, 110.71, 120–150 (m, 6C), 170.72, 171.17, 176.29. $^{19}$F NMR (282 MHz, CDCl$_3$): δ−143.56 (m, 2F), −151.08 (m, 2F); HRMS: C$_{27}$H$_{25}$F$_4$N$_3$O$_{11}$ requires M+1 at m/z 644.1503, found 644.1527.

EXAMPLE 2A (FIG. 4)

10-O-benzophenone-7-O-dansyl ginkgolide C (10a)

A solution of dansyl chloride (0.010 g, 0.035 mmol) in acetonitrile (0.3 mL) was added to a solution of 9a (0.020 g, 0.032 mmol) and DMAP (0.008 g, 0.063 mmol) in acetonitrile (1.5 mL). The reaction mixture was stirred for 16 h at room temperature, then a sat. aq. NH$_4$ClO-solution (2 mL) was added, and the mixture was extracted with EtOAc (3×5 mL). The combined organic phases were washed with sat. aq. NaCl-solution (3×15 mL), dried (MgSO$_4$) and removed in vacuo. The crude product was purified by flash column chromatography eluting with cyclohexane/acetone (2:1) to give the product as a slightly yellow solid (0.015 g, 56%). $^1$H NMR (400 MHz, DMSO-d$_6$): δ0.83 (s, tert-butyl), 1.09 (d, J=7.2, CH$_3$,), 1.94 (d, J=12.5, 8-H), 2.81 [m, 14-H and N(CH$_3$)$_2$], 4.26 (t, J=5.3, 1-H), 4.53 (d, J=5.4, 2-H), 4.79 (d, J=13.2, benzylic-H, 1H), 4.89 (dd, J=12.5, 4.0, 7-H), 5.19 (d, J=4.0, 6-H), 5.23 (s, 10-H), 5.46 (d, J=13.2, benzylic-H, 1H), 6.07 (d, J=5.3, 1-OH), 6.21 (s, 12-H), 6.51 (s, 3-OH), 7.28–7.30 (m, Ar—H, 1H), 7.50–7.70 (m, Ar—H, 7H), 7.79–7.82 (m, Ar—H, 4H), 8.18–8.20 (m, Ar—H, 2H), 8.54–8.56 (m, Ar—H, 1H); ). HRMS: C$_{46}$H$_{45}$NO$_{14}$S requires M+1 at m/z 868.2639, found 868.2642.

EXAMPLE 2B s10-O-benzophenone-1-O-dansyl ginkgolide C (10b)

Synthesized as 10a, but using 2 equivalents of dansyl chloride (instead of 1.1 equivalent) give rise to a 1:1 mixture of 10a and 10b. The two products were separated on analytical TLC giving 10b (0.008 g, 30%) as a slightly yellow solid. $^1$H NMR (400 MHz, DMSO-d$_6$): δ0.91 (s, tert-butyl), 1.16 (d, J=7.6, CH$_3$,), 1.78 (d, J=12.5, 8-H), 2.80 [s, N(CH$_3$)$_2$], 2.97 (q, J=7.6, 14-H), 4.22 (d, J=3.8, 1-H), 4.26 (m, 7-H), 4.57 (d, J=3.9, 6-H), 4.80 (d, J=13.2, benzylic-H, 1H), 5.20 (d, J=3.8, 2-H), 5.30 (s, 10-H), 5.31 (d, J=4.9, 7-OH), 5.49 (d, J=13.2, benzylic-H, 1H), 5.95 (s, 12-H), 5.98 (s, 3-OH), 7.25–7.27 (m, Ar—H, 1H), 7.54–7.79 (m, Ar—H, 11H), 8.18–8.24 (m, Ar—H, 2H), 8.47–8.49 (m, Ar—H, 1H); ). HRMS: C$_{46}$H$_{45}$NO$_{14}$S requires M+1 at m/z 868.2639, found 868.2668.

EXAMPLE 3 (FIG. 5)

10-O-benzoylbenzoic ginkgolide C (11)

4-Benzoylbenzoic acid (0.018 g, 0.08 mmol) and 2 (0.028 g, 0.07 mmol) was dissolved in THF (5 mL), and the mixture cooled to 0° C. 1-[3-(Dimethylamino)propyl]-3-ethylcarbodiimide HCl (EDC) (0.018 g, 0.092 mmol) and DMAP (0.002 g, 0.01 mmol) was added, and the reaction mixture stirred at 0° C. for 1 h, and continued overnight at room temperature. The solvent was removed in vacuo, the crude product dissolved in EtOAc (20 mL), and washed with a sat. 5% NaHCO$_3$-solution (20 mL) and brine (20 mL). The organic fraction was dried (MgSO$_4$) and the solvent evaporated in vacuo. The crude product was purified by flash column chromatography eluting with hexane/EtOAc (2:1) to give the product as white crystals (0.026 g, 62%). $^1$H NMR (400 MHz, CD$_3$OD): δ1.07 (s, tert-butyl), 1.26 (d, J=7.1, CH$_3$), 1.98–2.10 (m, 8-H and 7α-H), 2.30–2.36 (m, 7β-H), 3.12 (q, J=7.1, 14-H), 4.37 (d, J=6.5, 1-H), 4.55 (d, J=6.5, 2-H), 5.66 (d, J=3.2, 6-H), 6.32 (s, 10-H), 6.45 (s, 12-H), 7.54–7.58 (m, Ar—H, 2H), 7.67–7.69 (m, Ar—H, 1H), 7.80–7.83 (m, Ar—H, 2H), 7.86–7.88 (m, Ar—H, 2H), 8.42–8.44 (m, Ar—H, 2H). $^{13}$C NMR (100 MHz, CD$_3$OD): δ7.42, 28.22 (3C), 32.16, 37.27, 42.29, 49.42, 67.81, 70.64, 72.74, 74.42, 79.29, 83.64, 95.13, 100.51, 111.12, 128.73 (2C), 129.92 (2C), 130.17 (2C), 130.58 (2C), 131.61, 133.41, 137.06, 142.66, 164.56, 168.93, 171.41, 177.33, 196.48. HRMS: C$_{34}$H$_{31}$O$_{12}$ requires M+Na at m/z 655.1791, found 655.1790.

EXAMPLE 4A (FIG. 6)

7-trifluoromethanesulfonyloxy ginkgolide B (12)

Trifluoromethanesulfonic anhydride (0.2168 mL, 1.281 mmol) was added dropwise to a cooled solution of CH$_2$Cl$_2$ (2.84 mL) and pyridine (0.115 mL, 1.405 mmol) at −20° C. The solution was added dropwise to a solution of 3 (0.500 g, 1.134 mmol) in pyridine (4.83 mL) and the reaction was stirred for 2 hours at −20°. The reaction mixture was heated to room temperature and the solvent was in vacuo. The residue was dissolved in EtOAc (30 mL) and washed with 1M HCl (30 mL), and an aqueous, saturated NaCl solution (30, mL). The organic phase was dried (MgSO$_4$), then treated with activated carbon and filtered through Celite. The solvent was removed in vacuo and remaining solid was precipitated from heptane/methyl tert-butyl ether (2:1) to give a colorless solid. The solid was purified by flash column chromatography eluting with CHCl$_3$/MeOH/EtOAc (30:1:1, 20:1:1, 10:1:1) give the product as white crystals (0.61 g, 93%). $^1$H NMR (400 MHz, DMSO-d$_6$): δ1.11 (s, tert-butyl), 1.13 (d, J=9.6 Hz, CH$_3$,), 2.22 (d, J=16.5, 8-H), 2.82 (q, J=9.6 Hz, 14-H), 4.15 (dd, J=8.0, 5.9 Hz, 1-H), 4.73 (d, J=8.0 Hz, 2-H), 5.08 (d, J=7.4 Hz, 10-H), 5.24 (dd, J=16.5, 5.6 Hz, 7-H) 5.41 (d, J=5.6 Hz, 6-H), 5.54 (d, J=5.9 Hz, 1-OH), 6.20 (s, 12-H), 6.62 (s, 3-OH), 7.63 (d, J=7.4 Hz, 10-OH). $^{13}$C NMR (100 MHz, DMSO-d$_6$): δ9.1, 29.2 (3C), 32.6, 42.1, 49.0, 64.2, 68.1, 69.4, 74.4, 75.2, 84.0, 86.3, 93.2, 99.9, 109.4, 118.6 (q, $^1J_{CF}$=316.6, CF$_3$), 173.9, 176.9, 179.2. HRMS: C$_{21}$H$_{23}$F$_3$O$_{13}$S requires M+1 at m/z 573.0890, found 573.0872.

EXAMPLE 4B
7-Fluoro ginkgolide B (13)

7-trifluoromethanesulfonyloxy-ginkgolide B (12) (0.035 g, 0.061 mmol) and and tetrabutylammonium fluoride hydrate (0.038 g, 0.145 mmol) were dissolved in acetonitrile (0.2 mL) and heated at 80° C. for 30 min. The crude product was applied on an HPLC semi-preparative C18 column (7.8 mm×30 cmL) with a mobile phase of MeOH/H$_2$O (40:60) at a flow of 2 mL/min. The HPLC purified product was purified by flash column chromatography eluting with CHCl$_3$/MeOH (25:1) to give the final product as a white solid (0.016 g, 60%). $^1$H NMR (400 MHz, CD$_3$OD): δ1.25 (s, tert-butyl), 1.26 (d, J=7.1, CH$_3$), 1.94 (dd, J$_{HF}$=45.5, J=2.3, 8-H), 3.05 (q, J=7.1, 14-H), 4.24 (d, J=8.0, 1-H), 4.59 (d, J=8.0, 2-H), 5.18 (s, 10-H), 5.35 (d, J$_{HF}$=10.9, 6-H), 5.38 (dd, J$_{HF}$=48.8, J=2.3, 7-H), 6.14 (s, 12-H). $^{13}$C NMR (75 MHz, CD$_3$OD): δ7.0, 29.5 (3 C), 32.9, 42.4, 53.7 ($^2J_{CF}$=20.4), 68.8, 69.1, 71.5, 74.5, 79.5 ($^2J_{CF}$=36.0), 83.7, 91.7, 96.9 ($^2J_{CF}$=184.2), 98.8, 111.6, 171.2, 173.9, 177.1. HRMS: C$_{20}$H$_{23}$FO$_{10}$ requires M+1 at m/z 443.1354, found 443.1370.

EXAMPLE 4C
10-O-Methyl ginkgolide B (14)

To a suspension of ginkgolide B (0.030 g, 0.071 mmol) and K$_2$CO$_3$ (0.030 g, 0.212 mmol) in acetonitrile (0.5 mL) was added iodomethane (0.020 g, 0.141 mmol). The reaction mixture was heated under reflux for 30 min. This reaction resulted in a mixture of 10-methoxy-ginkgolide B and 1-methoxy ginkgolide B in a ratio of 4 to 1. 10-Methoxy-ginkgolide B was separated using an HPLC semi-preparative C18 column (7.8 mm×30 cmL) with a mobile phase of MeOH/H$_2$O (40:60) at a flow of 2 mL/min to give the final product as a white solid (0.017 g, 56%). $^1$H NMR (400 MHz, CD$_3$OD): δ1.14 (s, tert-butyl), 1.24 (d, J=7.1, CH$_3$), 1.90 (dd, J=14.2, 4.6, 8-H), 2.06 (td, J=13.9, 4.3, 7α-H), 2.25 (dd, J=13.6, 4.6, 7β-H), 3.05 (q, J=7.1, 14-H), 3.80 (s, OCH$_3$), 4.24 (d, J=7.4, 1-H), 4.57 (d, J=7.4, 2-H), 4.93 (s, 10-H), 5.43 (d, J=4.1, 6-H), 6.10 (s, 12-H). $^{13}$C NMR (75 MHz, CD$_3$OD): δ7.6, 7.0, 29.6 (3 C), 32.9, 37.6, 41.8, 48.8, 68.6, 70.5, 71.5, 74.4, 80.4, 82.2, 84.8, 90.9, 98.2, 110.3, 171.1, 173.0, 175.4. [Hu, L., Chen, Z., Xie, Y., Jiang, Y., & Zhen, H. (2000) *Bioorg. Med. Chem.* 8, 1515–1521]

EXAMPLE 4D
10-O-(2-Fluoroethyl) ginkgolide B (15)

Ginkgolide B (2) (0.031 g, 0.073 mmol) and 1-bromo-2-fluoroethane (0.102 g, 0.803 mmol) were dissolved in acetonitrile/DMF (4:10.25 mL) and heated at 80° C. for 30 min in the presence of tetrabutylammonium hydroxide (1M in MeOH, 0.125 mL). The crude product was a mixture of 10-fluoroethoxy ginkgolide B and 1-fluoroethoxy ginkgolide B in a 5 to 1 ratio (as determined by $^1$H NMR). The crude product was applied on an HPLC semi-preparative C18 column (7.8 mm i.d.×30 cmL) with a mobile phase of MeOH/H$_2$O (50:50) at a flow of 2 mL/min The HPLC purified product was purified by flash column chromatography eluting with CHCl$_3$/MeOH (50:1 and 25:1) to give the final product as a white solid (0.022 g, 63%). $^1$H NMR (400 MHz, CD$_3$OD): δ1.14 (s, tert-butyl), 1.25 (d, J=7.1, CH$_3$), 1.93 (dd, J=14.3, 4.7, 8-H), 2.10 (td, J=14.0, 4.3, 7α-H), 2.28 (dd, J=13.6, 4.7, 7β-H), 3.05 (q, J=7.1, 14-H), 3.90–4.01 (m, 1H, FCH$_2$CH$_2$O), 4.27 (d, J=7.4, 1-H), 4.53–4.78 (m, 3H, FCH$_2$CH$_2$O), 4.60 (d, J=7.4, 2-H), 5.15 (s, 10-H), 5.45 (d, J=4.1, 6-H), 6.13 (s, 12-H). $^{13}$C NMR (75 MHz, CD$_3$OD): δ7.1, 28.4 (3 C), 32.1, 37.1, 42.3, 49.6, 68.1, 70.4 ($^2J_{CF}$=21.0), 72.7, 74.5, 77.8 ($^1J_{CF}$=182.6), 81.7, 83.4, 83.9, 92.9, 99.6, 110.8, 171.5, 172.6, 177.3. HRMS: C$_{22}$H$_{27}$FO$_{10}$ requires M+1 at m/z 471.1667, found 471.1687.

EXAMPLE 5 (FIG. 7)
Synthesis of [$^3$H]-Ginkgolide B

Initially, nBu$_4$NB$^3$H$_4$ was synthesized as follows:

NaB$^3$H$_4$ (4.69 mg, 100 µmol specific activity 100 Ci/mmol, total activity 100 mCi) and NaOH (0.20 mg, 5 µmol) is dissolved in $^3$H$_2$O (100 µL, specific activity 5 Ci/g, total activity 500 mCi) in a vial. nBu$_4$NCl (18.53 mg, 66.7 µmol) in $^3$H$_2$O (100 µL, specific activity 5 Ci/g, total activity 500 mCi) is added and the reaction mixture is stirred for 1 min. CH$_2$Cl$_2$ (500 µL) is added to the vial, the mixture is shaken, the water layer is removed, MgSO$_4$ is added and the suspension stirred. The CH$_2$Cl$_2$ solution is filtered through MgSO$_4$ (in a syringe) into vial, and the solvent is removed by flowing nitrogen over the solution, and heating.

Figure 7:
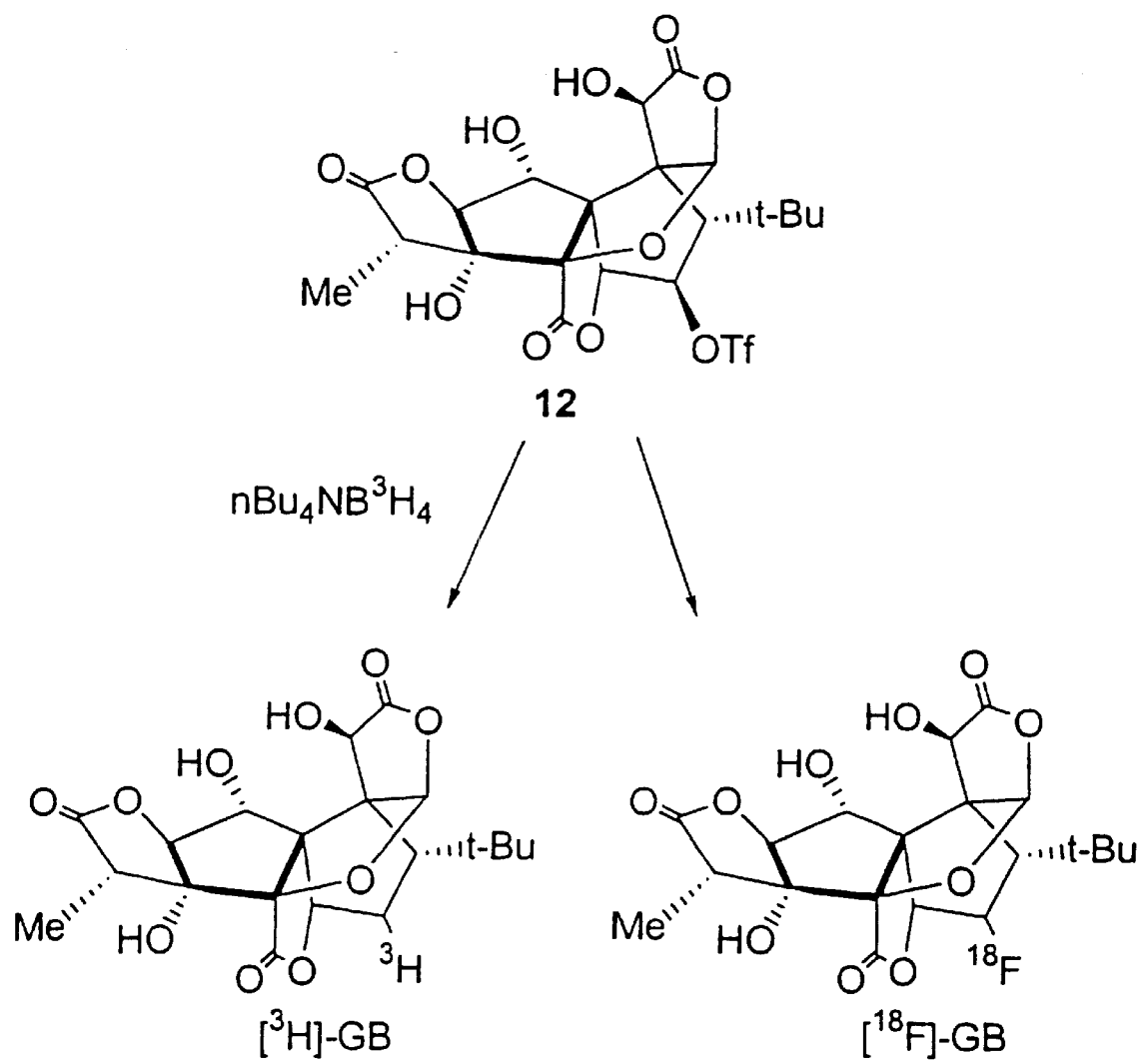
FIG. 7. [$^3$H]-Ginkgolide B ([$^3$H]-GB).

Then, the synthesis of [$^3$H]-Ginkgolide B followed (FIG. 7).

nBu$_4$NB$^3$H$_4$ (1.1 mg) in dry THF (20 µL) is added to a solution of 7-triflate-Ginkgolide C (14.5 mg, in dry THF (100 µL) precooled to 0° C. The mixture is stirred for 1.5 h at room temperature. MeOH (25 µL) is added, the mixture is shaken, and the solvent removed by flowing nitrogen over the solution, and heating. The residue is dissolved in acetonitrile (50 µL) and a mixture of H$_2$O/CH$_3$CN (1:1, 50 µL), and the solution is injected into the (preparative) HPLC (the product has a retention time of ca. 9.6 min.). Fractions is collected every 30 s (until 8 min.) then every 20 s, and an aliquot (5 µL) is taken into a scintillation vial, scintillation liquid is added and the vials is placed in a scintillation counter. Fractions corresponding to the peak of [$^3$H]-GB are collected and diluted with water, and passed through a C18 Sep-pak column, that is washed with water and [$^3$H]-GB is eluted with absolute ethanol into a vial, and the solvent is removed to give the product as a white solid (total activity 2.4 mCi, specific activity 3.8 mCi/µmol).

EXAMPLE 6
Bilobalide (6) Derivatives

Bilobalide derivatives having modifications at the 10-OH corresponding position are prepared following the procedures used herein to prepare Ginkgolide derivatives having modifications at the 10-OH position. Derivatization of Bilobalide (BB, 6) is performed as follows:

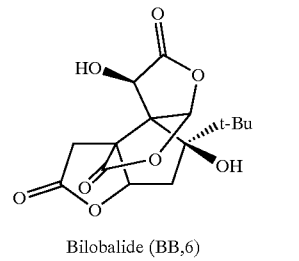

Bilobalide (BB,6)

R—X / base

X= leaving group
R= any alkyl, phenyl etc. group

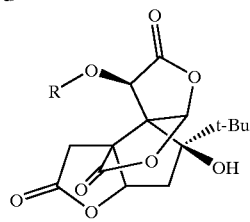

BIOLOGICAL TESTING

Radioligand Binding Assay

The radioligand binding assays were performed as previously described (47). In brief, membrane fractions from hearts and skeletal muscles of PAFR-Tg mice (50 µl suspension containing 121 fmol of PAFR) were mixed with 2 pmol of [$^3$H]-WEB in 50 µl of Buffer [25 mM Hepes/NaOH (pH 7.4), 0.25 M sucrose, 10 mM MgCl$_2$, 0.1% BSA], and the compound to be tested in 100 µl of buffer in a 96-well microplate in triplicate for each concentration. These mixtures were incubated at 25° C. for 90 min, upon which the receptor-bound [$^3$H]-WEB 2086 was filtered and washed with cold Buffer. The plates were then dried at 50° C. for at least 90 min., 25 µl of MicroScint-0 scintillation cocktail was added, and filters were placed in a TopCount microplate scintillation counter. Binding data were analyzed with the nonlinear curve-fitting program Microplate Manager III (Bio-Rad, Hercules, Calif.). Calculated IC$_{50}$ values were then converted to K$_i$ values using the Cheng-Prusoff correction (48), with the following equation: K$_i$=IC$_{50}$/(1+[L]/K$_D$), where [L] is the concentration of the radioligand, and K$_D$ is the previously determined dissociation constant for [$^3$H]-WEB 2086 (4.3 nM) (47). Non-specific binding was determined using methods as previously described (47).

RESULTS

Synthesis

A series of photoactivatable GB (2) and ginkgolide C (GC, 3) derivatives were synthesized. The design of GB derivatives 8a–c and GC derivatives 9a–c (FIG. 3) was based on previous SAR studies of ginkgolides which demonstrated that bulky aromatic substituents in the 10-OH position of GB (2) increases activity at the PAFR (40–42). Three different photoactivatable moieties, benzophenone, trifluoromethyldiazirine and tetrafluorophenyl azide (see 7a–c, FIG. 3) were chosen as they have been described as being among the most successful for labeling receptors and enzymes (51–53). Most importantly, upon irradiation these photoactivatable groups react with the receptor via different intermediates, namely, a radical, a carbene or a (singlet) nitrene for the benzophenone (7a), trifluoromethyldiazirine (7b) and tetrafluorophenyl azide (7c) moieties, respectively (51). Since it is essentially impossible to predict which group will be most readily incorporated into the receptor, use of these different groups increases the likelihood of a successful incorporation.

Figure 3:
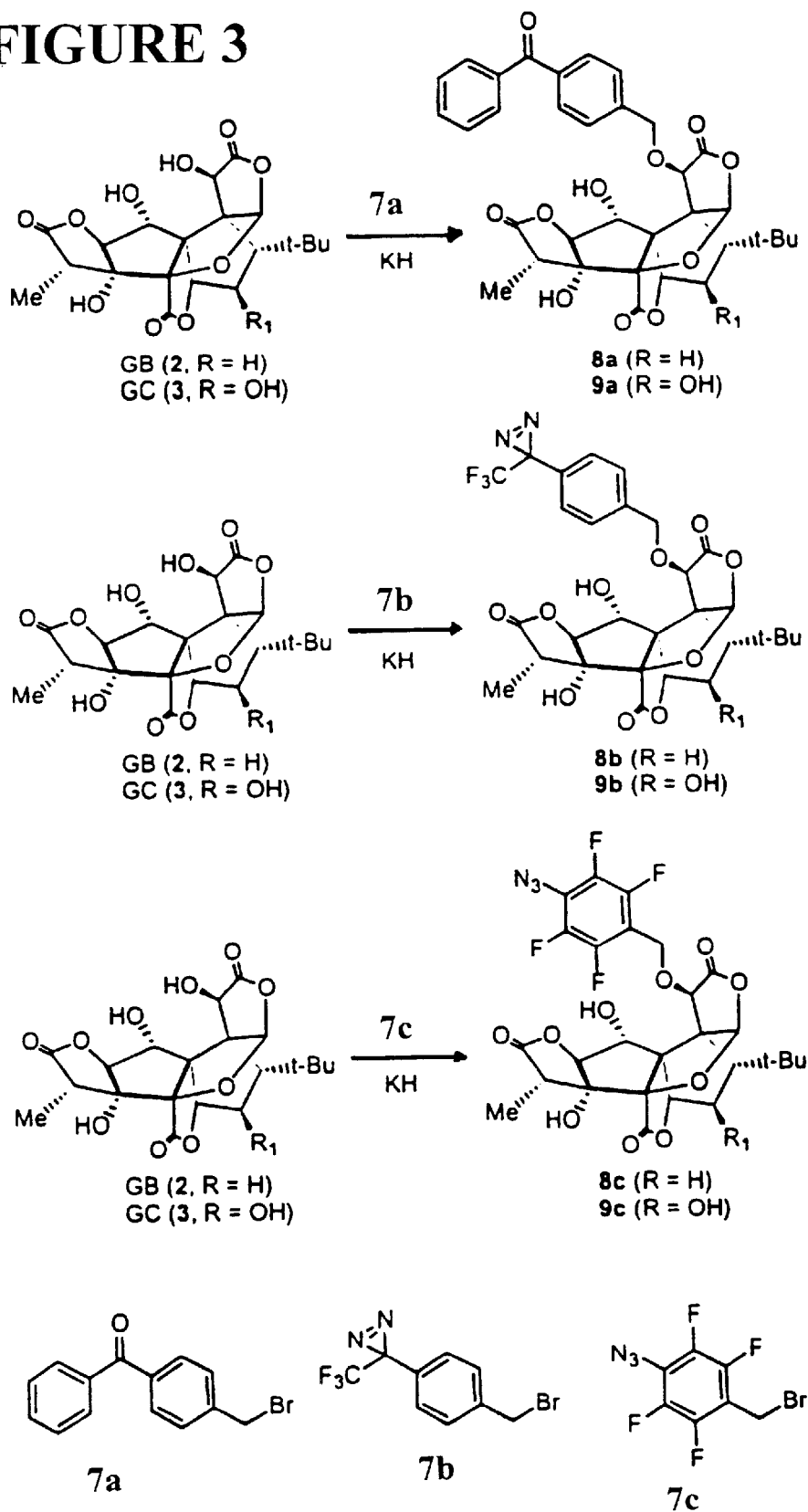
FIG. 3. Derivatives 8a–c and GC derivatives 9a–c.

Preparation of GB derivatives 8a–c and GC derivatives 9a–c was performed by reacting GB (2) and GC (3) with 4-(bromomethyl)benzophenone (7a), 3-(4-bromomethylphenyl)-3-trifluoromethyl-3H-diazirine (7b) and 1-azido-4-(bromomethyl)-2,3,5,6-tetrafluorobenzene (7c), respectively (FIG. 3). Benzophenone 7a was commercially available, whereas trifluoromethyldiazirine 7b(54, 55) and tetrafluorophenyl azide 7c(56–58) (FIG. 5) were synthesized, respectively, in 3 and 7 steps essentially as previously described. Ginkgolides GB (2) and GC (3) were derivatized almost exclusively at 10-OH when potassium hydride (KH) was used as base, as was previously shown for GB (2) (40), whereas other bases were less selective, giving rise to products derivatized at 1-OH as well. Generally, the position of the substituent was determined from the coupling systems of the appropriate protons in DMDO-d$_6$, as well as by COSY NMR spectra. The relative chemical shift of 12-H in DMSO-d$_6$ can also be used in differentiating 1- and 10-OH substitutions (42).

Figure 4:
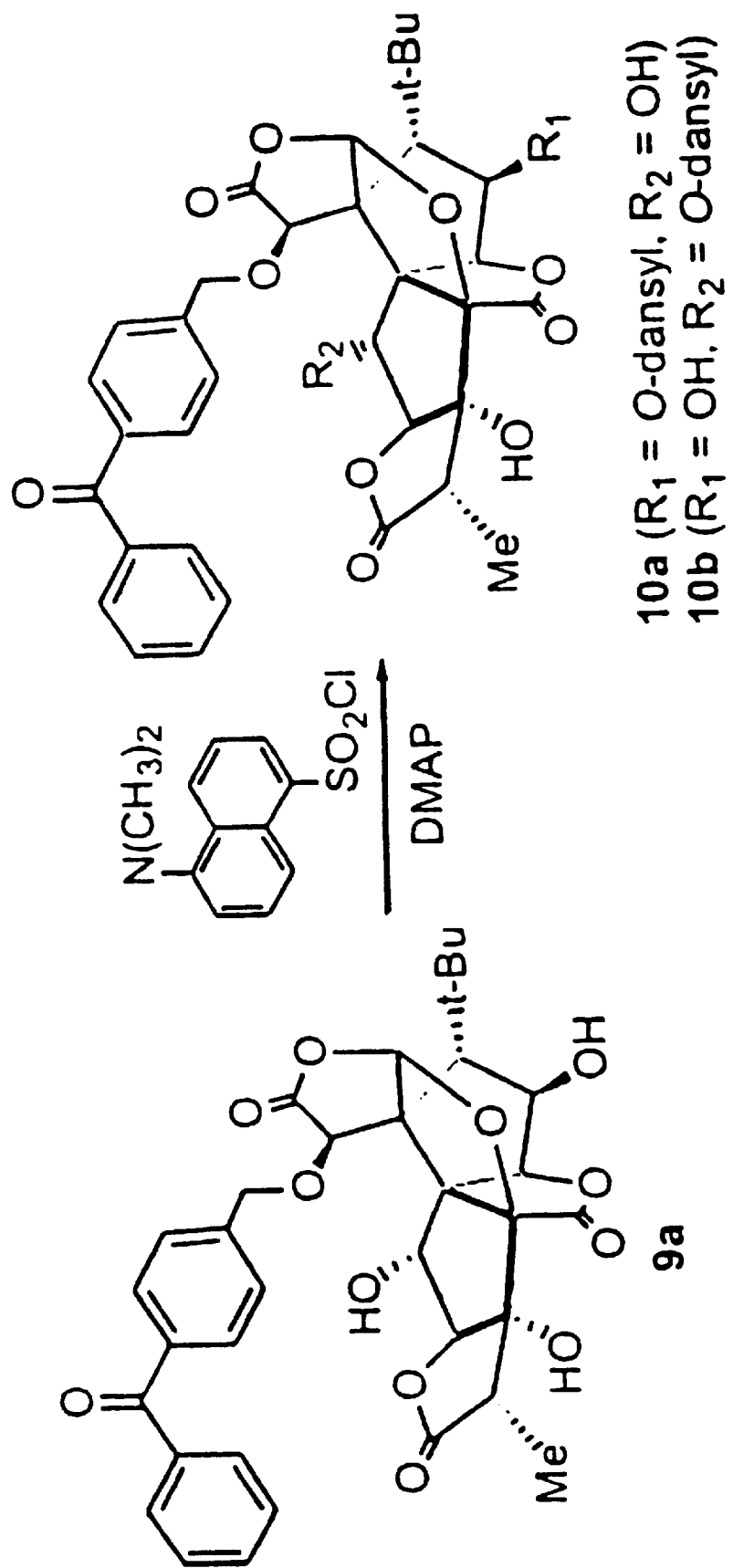
FIG. 4. 10-O-benzophenone-7-O-dansyl GC (10a) and 10-O-benzophenone-1-O-dansyl GC (10b).
Figure 5:
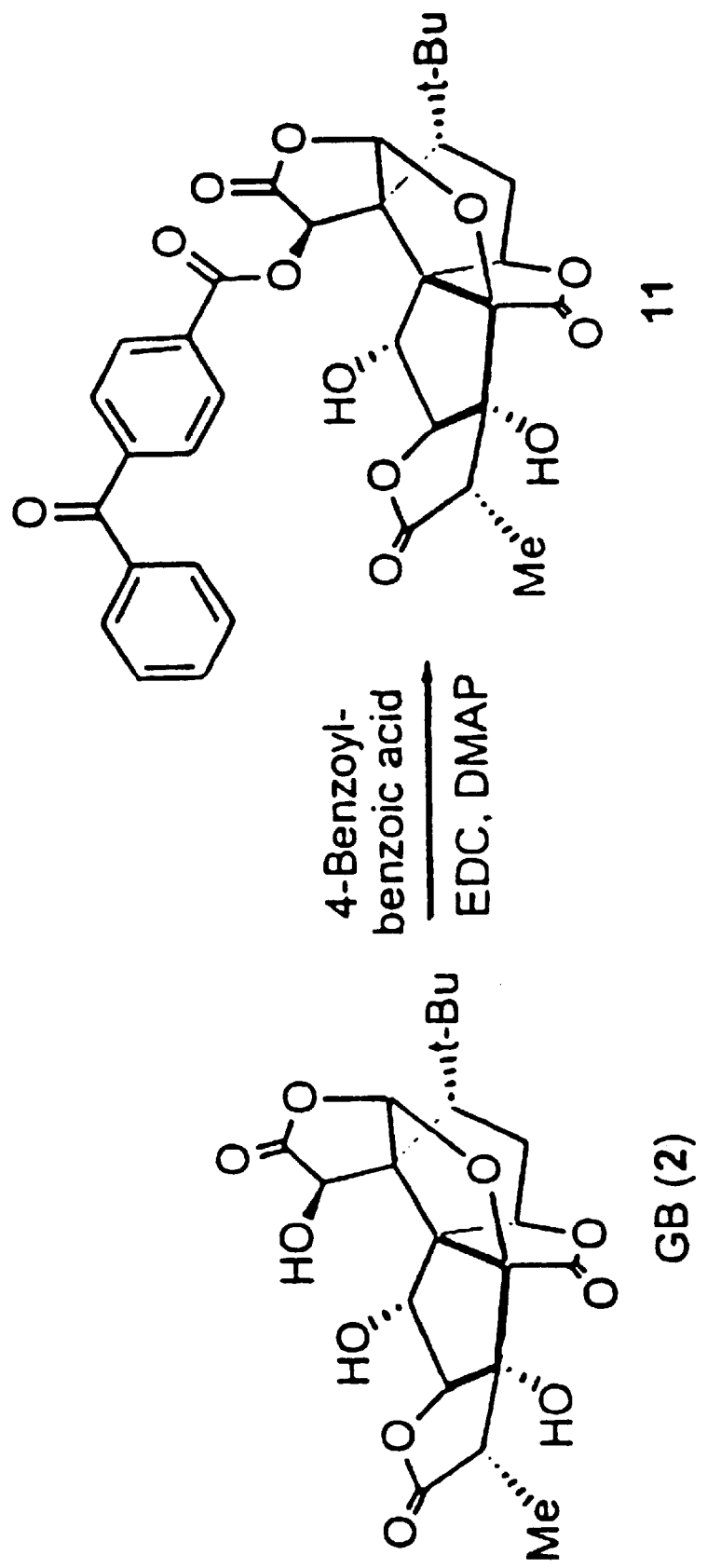
FIG. 5. 10-benzophenonecarbonyl GC (11).

GC derivatives 9a–c can be reacted further to incorporate fluorescent groups; for example, benzophenone derivative 9a was reacted with one equivalent of 5-(dimemethylamino)naphthalene-sulfonyl chloride (dansyl chloride), to give 10-O-benzophenone-7-O-dansyl GC (10a) with almost exclusive reaction at 7-OH (FIG. 4). Interestingly, increasing the amount of dansyl chloride to two equivalents gave 10-O-benzophenone-1-O-dansyl GC (10b) as well as (10a) in a 1:1 ratio. The coupling of GB (2) with 4-benzoylbenzoic acid using 1-[3-(dimethylamino)propyl]-3-ethylcarbodiimide HCl (EDC) and 4-dimethylaminopyridine (DMAP) occurred exclusively at 10-OH to give 10-benzophenonecarbonyl GC (11) in good yield (FIG. 5). In 10-benzophenonecarbonyl GC (11) the photoactivatable benzophenone moiety, as in the case of 8a and 9a, is linked to the ginkgolide skeleton through an ester linkage. Upon incorporation into the receptor, the ester group can be aminolysed with a fluorescent amine such as 1-pyrenemethylamine, thus avoiding the use of radioactivity for photolabeling and sequencing (59).

Figure 6:
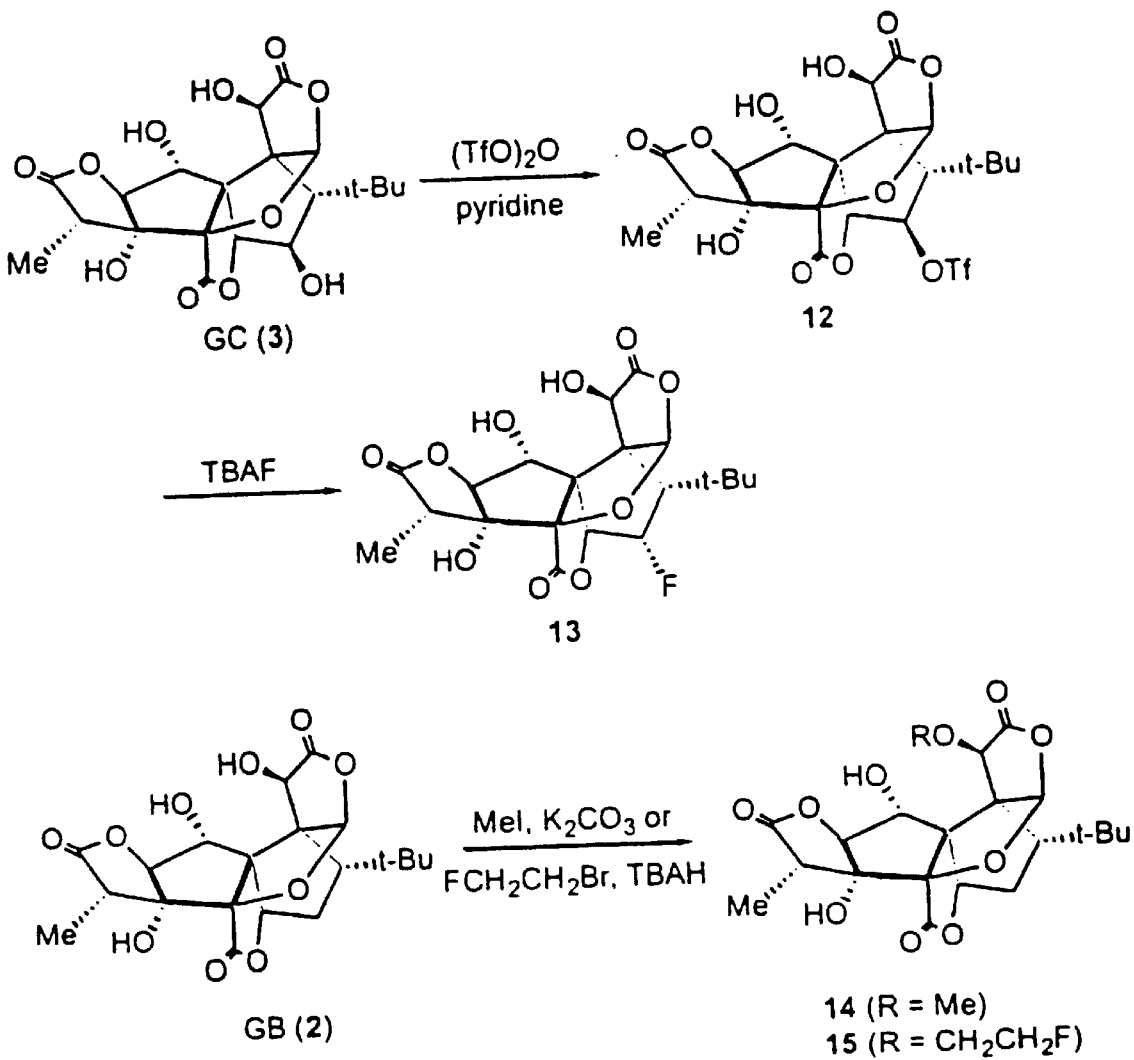
FIG. 6. 7-fluoro analog of GB (13), 10-O-methyl GB (14), and 10-O-(2-fluoroethyl) GB (15).

For positron emission tomography (PET) studies derivatives labeled with [$^{18}$F]- and [$^{11}$C] possessing half lives of 110 min and 20 min, respectively, will be used. In the present work, preparation of the corresponding non-radioactive analogs has been performed. Compound 13, a 7-fluoro analog of GB (2) which can ultimately be labeled with [$^{18}$F], was prepared by nucleophilic substitution of 7-O-triflate intermediate 12 with tetrabutylammonium fluoride (TBAF) (FIG. 6). As expected for nucleophilic substitution, NMR showed the relative stereochemistry at C-7 to be reversed compared to GC (3). Intermediate 12 was prepared by reaction of GC (3) with trifluoromethanesulphonic anhydride [(CF$_3$SO$_2$)$_2$O] with remarkable selectivity for the 7-OH, as no substitutions at other hydroxyl groups was observed (60). Two other potential PET-ligands, which can be labeled with [$^{11}$C], were prepared by selective reaction of the 10-OH of GB (2) with either methyl iodide or 2-bromoethyl fluoride to give 10-O-methyl GB (14) and 10-O-(2-fluoroethyl) GB (15), respectively (FIG. 6). Upon reacting GB (2) with methyl iodide, reaction at 1-OH could not be avoided, the 10-OH:1-OH product ratio being highly sensitive to the use of the appropriate base, e.g., K$_2$CO$_3$ gave primarily the 10-substituted analog, whereas tetrabutylammonium hydroxide (TBAH) gave mainly the 1-substituted derivative.

Pharmacology

Figure 2:
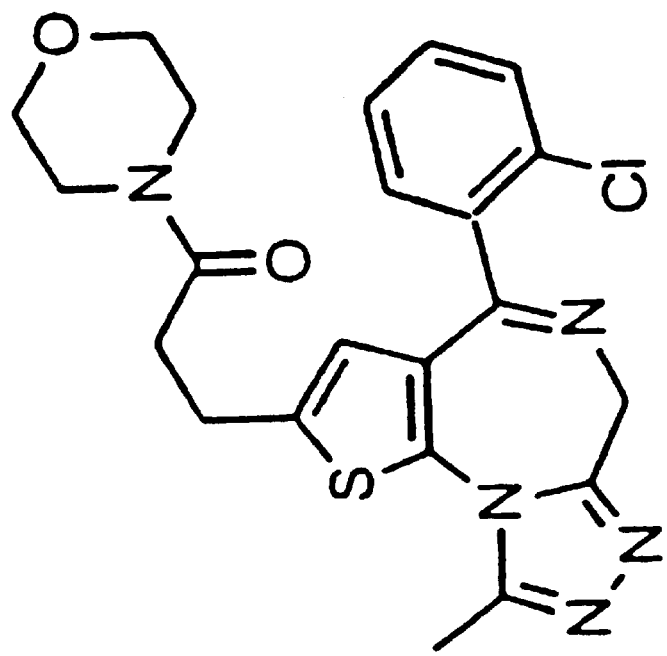
Figure 2:
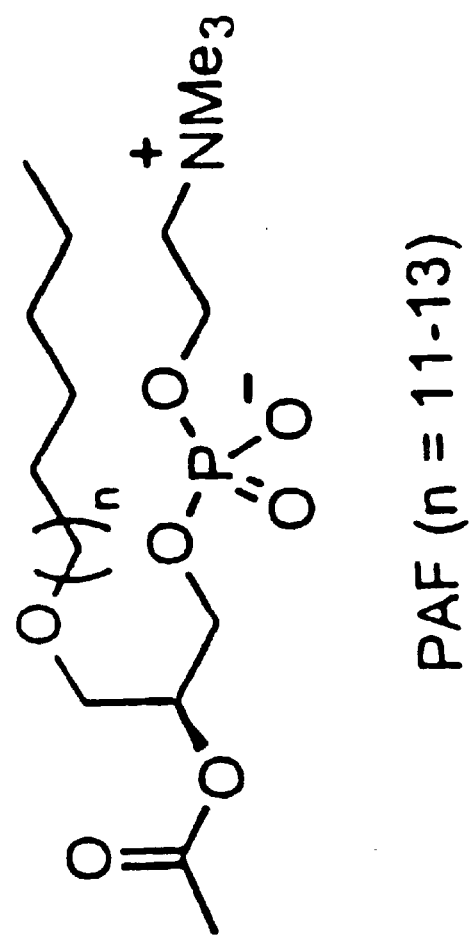

The native terpene trilactones (1–6), as well as ginkgolide derivatives 8a–c, 9a–c, 10a, 10b, 11 and 13–15 were tested for their ability to bind to PAFR using radioligand binding assays with membrane fractions from hearts and skeletal muscles of PAFR transgenic mice (47). Initially compounds were tested in concentrations of 5 µM against [$^3$H]-WEB 2086 (FIG. 2), a potent, competitive PAFR antagonist and [$^3$H]-PAF; the compounds were generally less potent against [$^3$H]-PAF, but the relative potencies were comparable with the two radioligands. The degree of non-specific binding was determined to be ca. 50% for [$^3$H]-PAF and less than 5% for [$^3$H]-WEB 2086. Accordingly, the assays were performed using [$^3$H]-WEB 2086 rather than [$^3$H]-PAF as the radioligand, mainly due to the high degree of non-specific binding of the latter.

All compounds were dissolved in DMSO to obtain 5 mM stock solutions of test compounds. Examination of the effect of DMSO on the binding of [$^3$H]-WEB 2086 revealed that up to 1% DMSO (final concentration) was acceptable, but 1–2.5% resulted in a slight inhibition of [3H]-WEB 2086 binding. Generally this caused no problem; however, with very weakly binding compounds the relatively high DMSO concentration in solutions above 100 μM had a small inhibitory effect, thus leading to a slight overestimation of their potencies. Previous studies have reported problems specifically associated with the solubilization of ginkgolides in DMSO (61), but similar problems were not observed in the present study.

Native ginkgolides (1–5) and bilobalide (6) were tested with the cloned PAFR (FIG. 3A and Table 1). GB (2) was the most potent compound with a $K_i$ value of 0.56 μM, while GA (1) was slightly less potent with a $K_i$ of 1.46 μM. GC (3) and ginkgolide J (GJ, 4) were significantly less potent, while ginkgolide M (GM, 5) and bilobalide (6) both had $K_i$ values larger than 50 μM. The GB-derived photoactivatable compounds 8a–c and 11 with $K_i$ values in the range 0.09–0.15 μM (FIG. 3B and Table 2) were all more potent than GB (2), while compounds 9a–c derived from GC (3) with $K_i$ values of 0.47–0.79 μM were equipotent to GB (2) (FIG. 3C and Table 2), despite the fact that GC (3) itself is only weakly potent. Besides proving that aromatic groups linked to 10-OH enhance activity in both GB (2) and GC (3) derivatives, these results also indicate that the specific type of photoactivatable group was less important. Derivatives 10a and 10b possessing a fluorescent dansyl group at either 1- or 7-OH were both less potent than 10-O-benzophenone GC (9a) without the dansyl group (FIG. 3D). However, an important difference was observed in the activities of the two; the 1- and 10-disubstituted analog (10b) was ca. four times more potent than the 7- and 10-disubstituted analog (10a) (Table 2).

TABLE 1

The $K_i$ values of the native terpene trilactones.

| Compound | $K_i$ (μM)$^a$ | Compound | $K_i$ (μM)$^a$ |
|---|---|---|---|
| GA (1) | 1.46 | GJ (4) | 9.90 |
| GB (2) | 0.56 | GM (5) | >50 |
| GC (3) | 12.6 | BB (6) | >50 |

$^a$Inhibition of [$^3$H]-WEB 2086 binding.

TABLE 2

The $K_i$ values of the synthesized derivatives.

| Compound | $K_i$ (μM)$^a$ | Compound | $K_i$ (μM)$^a$ |
|---|---|---|---|
| 8a | 0.15 | 10a | 3.94 |
| 8b | 0.15 | 10b | 0.96 |
| 8c | 0.09 | 11 | 0.13 |
| 9a | 0.58 | 13 | 0.99 |
| 9b | 0.47 | 14 | 3.16 |
| 9c | 0.79 | 15 | 4.87 |

$^a$Inhibition of [$^3$H]-WEB 2086 binding.

Finally the potential PET analogs 13–15 were tested. The fluorinated analog 13 had a $K_i$ value of 0.99 μM (Table 2), thus being almost equipotent with the native compound GB (2). The C-10 derivatized compounds 10-O-methyl GB (14) and 10-O-(2-fluoroethyl) GB (15) were both significantly less potent than GB (2) with $K_i$ values of 3.16 and 4.87 μM for 14 and 15, respectively (Table 2).

DISCUSSION

Nine analogs (8a–c, 9a–c, 10a, 10b and 11) with photoactivatable groups, and in the case of 10a and 10b with fluorescent dansyl groups as well, have been prepared from native ginkgolides GB (2) and GC (3) by selective derivatizations of the hydroxyl groups. Furthermore, we have prepared three analogs (13–15), the radioactive versions of which will be used for PET studies. For the synthesis of 7-O-triflate intermediate 12, reaction of GC (3) with sulfonic anhydride gave rise to remarkable selectivity at 7-OH (60). 10-O-Methyl GB (14) and 10-O-(2-fluoroethyl) GB (15) were synthesized by derivatization of GB (2), indicating that when the appropriate combination of alkylating agent and base is used, even small aliphatic groups react preferentially at the 10-OH. Generally, the increased reactivity of the 1-OH and 10-OH compared to 7-OH, has been rationalized by hydrogen-bonding between 1-OH and 10-OH (62), but this does not explain the interesting selectivity for the 10-OH position in reactions with benzyl bromide derivatives. Notably, reaction of GC (3) with a bulky silyl chloride protection group occurs exclusively at the 1-OH of GC (63).

All native terpene trilactones as well as the derivatized compounds were investigated with respect to their binding to cloned PAFR isolated from transgenic mice (FIG. 3A). Previous SAR studies of PAFR antagonism with terpene trilactones and derivatives was performed by monitoring inhibition of PAF-induced rabbit platelet aggregation. GB (2) has generally been reported to be a potent antagonist of the PAFR based on the latter assay with an $IC_{50}$ value around 0.2 μM (40–42).

GM (5) has only been found in the root bark of the G. biloba tree (3) and is not readily available. Thus, the interaction between PAFR and GM (5) has not previously been reported. The remaining terpene trilactones are all found in the leaf of G. biloba. However 5, lacking the hydroxyl group at C-3, was devoid of PAFR binding at the concentrations tested. Generally the activities of GC (3), GJ (4) and GM (5) with hydroxyl groups at C-7, compared to the activity of GA (1) and GB (2) lacking the 7-OH, showing that the 7-OH is not necessary for binding to PAFR, whereas hydroxyl groups at other positions appear to be less important. The study also confirmed that bilobalide (6), a terpene trilactone with only one five-membered carbocycle and three lactones, is not active in concentrations up to 100 μM (Table 1).

The seven photolabile analogs, GB derivatives 8a–c and 11 and GC derivatives 9a–c, with aromatic substituents at 10-OH all improved the affinity to the PAFR relative to the activities of GB (2) and GC (3) (Table 2). This is in agreement with previous SAR studies of GB (2) (40–42), as well as a 3D-QSAR study on ginkgolides (64). However, it is interesting to note that aromatic substitutions at 10-OH of GC (3) as in compounds 9a–c, improve the affinity to PAFR ca. 20 fold (FIG. 3C) thus making them equipotent to GB (2), while the same substitutions in GB (2) increases the affinity only 6-fold (FIG. 3B). Furthermore, the similar affinities of GB derivatives 8a–c (FIG. 3B) and 11 and GC derivatives 9a–c (FIG. 3C), respectively, implies that it is the steric bulk or the lipophilicity of the substituents, rather than the specific functional groups that are important for the increase in affinity (Table 2).

GC derivatives 10a and 10b (FIG. 4) with dansyl groups at 7-OH and 1-OH are less potent and equipotent, respectively to their parent compound, 10-O-benzophenone-GC (9a) (FIG. 3D). In compound 10a, which is ca. 6 times less active than 9a (Table 2), the bulk at the 7 position seems to be responsible for the reduction in affinity. The fact that compound 10b is equipotent to 9a suggests that once a bulky aromatic group occupies this area, further aromatic groups neither increase nor decrease the affinity.

The 7-fluoro GB (13, FIG. 6) was essentially equipotent to GB (2), and ca. 10 times more potent than GC (3); thus, the [$^{18}$F]-labeled analog of 13 could be a useful probe for visualizing the PAFR binding sites in mammalian brain. Furthermore, 13 could be used for probing interactions of [$^{18}$F]-13 with targets other than the PAFR. The substitution at C-7 of ginkgolides is critical for PAFR binding affinity; generally a β-OH group significantly decreases binding affinity, as in GC (3), GJ (4) and GM (5), while substitution with a dansyl group at 7-OH, as in 10a, reduces this activity further. However, an a-fluorine at C-7 position has an affinity 10-fold higher than that of GC (3) and comparable to that of GB (2). The inverted stereochemistry at C-7, rather than electronic or steric effects of the fluorine substitution, may account for the enhanced activity.

Others who have made, or purported to make, Ginkgolide derivatives with modifications at C-7 did not appreciate the importance of stereochemistry at the C-7 position (65–67). The data presented shows the unexpected improvement in PAFR binding affinity when the C-7 substituent is an α-substituent. Thus, Ginkgolide derivatives having both an α-substituent at C-7 and a bulky or lipophillic substitution at 10-OH are expected to have yet further improved activity.

The two derivatives bearing alkyl substituents at C-10 of GB, 10-O-methyl GB (14) and 10-O-(2-fluoroethyl) GB (15), are both significantly less potent than GB (2). Thus, although the [$^{11}$C]-labeled derivatives are not suited for examination of interactions with the PAFR, both ligands should be useful for visualizing targets for ginkgolides in the brain, other than PAFR. Of course, all of the described compounds are expected to be useful for visualizing their targets in the brain, other than PAFR.

In conclusion, investigation of the effect of terpene trilactones isolated from *G. biloba* on the cloned PAFR have demonstrated that amongst the native compounds, GA (1) and GB (2) are the most potent. A series of photoactivatable analogs have been prepared, and PAFR binding assays showed that most of these analogs were more potent antagonists than their parent compounds, thus providing promising candidates for studies of the interaction of ginkgolides with the PAFR. The gingkolide derivative containing both a photoactivatable and a fluorescent group, compound 10b, retained affinity to PAFR, and could therefore be useful in photolabeling and subsequent sequencing studies. Finally, the syntheses and assays of analogs that can be radiolabeled and used for PET studies have been described; in particular the radiolabeled derivative of 7-fluoro GB (13) could be a useful probe for in vivo PET studies of the PAFR, as well as potential new targets for ginkgolides.

REFERENCES

1. Drieu, K., Jaggy, H. (2000) in *Medicinal and Aromatic Plants-Industrial Profiles: Ginkgo biloba*, ed. van Beek, T. A. (Harwood Academic Publishers, Amsterdam), Vol. 12, pp. 267–277.
2. Hasler, A. (2000) in *Medicinal and Aromatic Plants-Industrial Profiles: Ginkgo biloba*, ed. van Beek, T. A. (Harwood Academic Publishers, Amsterdam), Vol. 12, pp. 109–142.
3. Nakanishi, K. (1967) *Pure Appl. Chem.* 14, 89–113 and references therein.
4. Okabe, K., Yamada, K., Yamamura, S., & Takada, S. (1967) *J. Chem. Soc. C*, 2201–2206.
5. Nakanishi, K., Habaguchi, K., Nakadaira, Y., Woods, M. C., Maruyama, M., Major, R. T., Alauddin, M., Patel, A. R., Weinges, K., & Bäher, W. (1971) *J. Am. Chem. Soc.* 93, 3544–3546.
6. Weinges, K. Hepp, M., & Jaggy, H. (1987) *Liebigs Ann. Chem.* 521–526.
7. DeFeudis, F. V. & Drieu, K. (2000) *Curr. Drug Targets*, 1, 25–58.
8. Logani, S., Chen, M. C., Tran, T., Le, T., & Raffa, R. B. (2000) *Life Sci.* 67, 1389–1396.
9. Oken, B. S., Storzbach, D. M., & Kaye, J. A. (1998) *Arch. Neurol.* 55, 1409–1415.
10. Kleijnen, J. & Knipschild, P. (1992) *Lancet* 340, 1136–1139.
11. Søholm, B. (1998) *Adv. Nat. Ther.* 15, 54–65.
12. Diamond, B. J., Shiflett, S. C., Feiwel, N., Mathies, R. J., Noskin, O., Richards, J. A., & Schoenberger, N. E. (2000) *Arch. Phys. Med. Rehabil.* 81, 668–678.
13. van Dongen, M. C. J. M., van Rossum, E., & Knipschild P. (2000) in *Medicinal and Aromatic Plants-Industrial Profiles: Ginkgo biloba*, ed. van Beek, T. A. (Harwood Academic Publishers, Amsterdam), Vol. 12, pp. 385–442.
14. Le Bars, P. L., Katz, M. M., Berman, N., Itil, T. M., Freedman, A. M., & Schatzberg, A. F. (1997) *J. Am. Med. Assoc.* 278, 1327–1332.
15. Kanowski, S., Hermann, W. M., Stephan, K., Wierich, W., & Horr, R. (1996). *Pharmacopsychiatry* 29, 47–56.
16. Watanabe, M. H., Wolffram, S., Ader, P., Rimbach, G., Packer, L., Maguire, J. J., Shultz, P. G., & Gohil, K. (2001) *Proc. Natl. Acad. Sci. USA* 98, 6577–6580.
17. Kennedy, D. O., Scholey, A. B., & Wesnes, K. A. (2000) *Psychopharmacol.* 151, 416–423.
18. Polich, J. & Gloria, R. (2001) *Hum. Psychopharmacol. Clin. Exp.* 16, 409–416.
19. Rigney, U., Kimber, S., & Hindmarch, I. (1999) *Phytother. Res.* 13, 408–415.
20. Stough, C., Clarke, J., Lloyd, J., & Nathan, P. J. (2001) *Int. J. Neuropsychopharmacol.* 4, 131–134.
21. Braquet, P., Spinnewyn, B., Braquet, M., Bourgain, R. H., Taylor, J. E., Etienne, A., & Drieu, K. (1985) *Blood Vessels* 16, 559–572.
22. Ishii, S. & Shimizu, T. (2000) *Prog. Lipid. Res.* 39, 41–82.
23. Prescott, S. M., Zimmerman, G. A., Stafforini, D. M., & McIntyre, T. M. (2000) *Annu. Rev. Biochem.* 69, 419–445.
24. Shukla, S. D. (1996) *Biomembranes* 2B, 463–479.
25. Bito, H., Nakamura, M., Honda, Z., Izumi, T., Iwatsubo, T., Seyama, Y., Ogura, A., Kudo, Y., & Shimizu, T. (1992) *Neuron* 9, 285–294.
26. Mori, M., Aihara, M., Kume, K., Hamanoue, M., Kohsaka, S., & Shimizu, T. (1996) *J. Neurosci.* 16, 3590–3600.
27. Kroegel, C., Kortsik, C., Kroegel, N. & Matthys, H. (1992) *Drugs Aging* 2, 345–355.
28. Perry, S. W., Hamilton, J. A., Tjoelker, L. W., Dbaibo, G., Dzenko, K. A., Epstein, L. G., Hannun, Y., Whittaker, J. S., Dewhurst, S., & Gelbard, H. A. (1998) *J. Biol. Chem.* 273, 17660–17664.
29. Kato, K., Clark, G. D., Bazan, N. G., & Zorumski, C. F. (1994) *Nature* 367, 175–179.
30. Kornecki, E., Wieraszko, A., Chan, J. C., & Ehrlich, Y. H. (1996) *J. Lipid Mediators Cell Signal.* 14, 115–126.
31. Chen, C., Magee, J. C., Marcheselli, V., Hardy, M., & Bazan, N. G. (2001) *J. Neurophysiol.* 85, 384–390.

32. Kobayashi, K., Ishii, S., Kume, K., Takahashi, T., Shimizu, T., & Manabe, T. (1999) *Eur. J. Neurosci.* 11, 1313–1316.
33. Smith, P. F., Maclennan, K., & Darlington, C. L. (1996) *J. Ethnopharmacol.* 50, 131–139.
34. Smith, P. F. & Maclennan, K. (1999) *Curr. Opin. Anti-Inflamm. Immuno. Invest. Drugs* 1, 205–218.
35. Corey, E. J. & Ghosh, A. K. (1988) *Tetrahedron Lett.* 29, 3205–3206.
36. Corey, E. J., Kang, M. C., Desai, M. C., Ghosh, A. K., & Houpis, I. N. (1988) *J. Am. Chem. Soc.* 110, 649–651.
37. Corey, E. J. & Su, W. G. (1987) *J. Am. Chem. Soc.* 109, 7534–7536.
38. Corey, E. J. & Gavai, A. V. (1989) *Tetrahedron Lett.* 30, 6959–6962.
39. Corey, E. J. & Rao, K. S. (1991) *Tetrahedron Lett.* 32, 4623–4626.
40. Park, P.-U., Pyo, S., Lee, S.-K., Sung, J. H., Kwak, W. J., Park, H.-K., Cho, Y.-B., Ryu, G. H., & Kim, T. S. (1996) U.S. Pat. No. 5,541,183. See, also, U.S. Pat. No. 5,466,829.
41. Hu, L., Chen, Z., Cheng, X., & Xie, Y. (1999) *Pure Appl. Chem.* 71, 1153–1156.
42. Hu, L., Chen, Z., Xie, Y., Jiang, H., & Zhen, H. (2000) *Bioorg. Med. Chem.* 8, 1515–1521.
43. Hu, L., Chen, Z., Xie, Y., Jiang, Y., & Zhen, H. (2000) *J. Asian Nat. Prod. Res.* 2, 103–110.
44. Hu, L., Chen, Z., & Xie, Y. (2001) *J. Asian Nat. Prod. Res.* 3, 219–227.
45. Ishii, S., Nagase, T., Tashiro, F., Ikuta, K., Sato, S., Waga, I., Kume, K., Miyazaki, J., & Shimizu, T. (1997) *EMBO J.* 16, 133–142.
46. Bradford, M. M. (1976) *Anal. Biochem.* 72, 248–254.
47. Shindou, H., Ishii, S., Uozumi, N., & Shimizu, T. (2000) *Biochem. Biophys. Res. Commun.* 271, 812–817.
48. Cheng, Y. & Prusoff, W. H. (1973) *Biochem. Pharmacol.* 22, 3099–3103.
49. Aoki, Y., Nakamura, M., Kodama, H., Matsumoto, T., Shimizu, T. & Noma, M. (1995) *J. Immunol. Methods*, 186, 225–231.
50. Fukunaga, K., Ishii, S., Asano, K., Yokomizo, T., Shiomi, T., Shimizu, T. & Yamaguchi, K. (2001) *J. Biol. Chem.*, 276, 43025–43030.
51. Dorman, G. & Prestwich, G. D. (2000) *Trends Biotech.* 18, 64–77.
52. Flemming, S. A. (1995) *Tetrahedron* 51, 12479–12520.
53. Kotzyba-Hilbert, F., Kapfer, I., & Goeldner, M. (1995) *Angew. Chem. Int. Ed. Engl.* 34, 1296–1312.
54. Nassal, M. (1983) *Liebigs Ann. Chem.* 1510–1523.
55. Nassal, M. (1984) *J. Am. Chem. Soc.* 106, 7540–7545.
56. Keana, J. F. W. & Cai, S. X. (1990) *J. Org. Chem.* 55, 3640–3647.
57. Lei, H., Marks, V., Pasquale, T., & Atkinson, J. K. (1998) *Bioorg. Med. Chem. Lett.* 8, 3453–3458.
58. Lei, H. & Atkinson, J. (2000) *J. Org. Chem.* 65, 2560–2567.
59. Li, H., Liu, Y., Fang, K., & Nakanishi, K. (1999) *Chem. Commun.* 365–366.
60. Teng, B.-P. (1997) U.S. Pat. No. 5,599,950. See, also, GB 2 288 599 A.
61. Maclennan, K. M., Smith, P. F., & Darlington, C. L. (1996) *Neurosci. Res.* 26, 395–399.
62. Corey, E. J.; Rao, K. S. & Ghosh, A. K. (1992) *Tetrahedron Lett.* 33, 6955–6958.
63. Weinges, K. & Schick, H. (1991) *Liebigs Ann. Chem.* 81–83.
64. Chen, J., Hu, L., Jiang, H., Gu, J., Zhu, W., Chen, Z., Chen., K., & Ji, R. (1998) *Bioorg. Med. Chem. Lett.* 8, 1291–1296.
65. Pietri et al., *PCT International Publication* WO 99/52911.
66. Ceazaux et al., UK Patent Application GB 2 288 599 A.
67. Vasella et al., U.S. Pat. No. 6,143,725.

What is claimed is:

1. A compound having the structure:

wherein $R_1$ is H, OH, a photoactivatable moiety, a fluorescent moiety, or a radioactive moiety;

wherein $R_2$ is H, OH, a photoactivatable moiety, a fluorescent moiety, or a radioactive moiety;

wherein $R_3$ is H or OH;

wherein $R_4$ is H, OH, a photoactivatable moiety, a fluorescent moiety, or a radioactive moiety; and wherein at least one of $R_1$, $R_2$, $R_3$, or $R_4$ is a photoactivatable moiety, a fluorescent moiety, or a radioactive moiety, or an optically pure enantiomer of the compound.

2. The compound of claim 1, wherein $R_1$ is a fluorescent moiety and each of $R_2$ and $R_4$ is H or OH.

3. The compound of claim 1, wherein $R_2$ is a fluorescent moiety or a radioactive moiety and each of $R_1$ and $R_4$ is H or OH.

4. The compound of claim 1, wherein $R_4$ is a photoactivatable moiety or a radioactive moiety and each of $R_1$ and $R_2$ is H or OH.

5. The compound of claim 1, wherein the photoactivatable moiety is a phenylazide, a purine or pyrimidine azides, a diazoacetate, a diazoketone, a nitrobenzene, or an aryldiazonium salt.

6. The compound of claim 1, wherein the photoactivatable moiety is benzophenone, trifluoromethyldiazirine tetrafluorophenyl, 8-azidoadenosine, 2-azidoadenosine, or 3H, 3-aryldiazirine.

7. The compound of claim 1, wherein the fluorescent moiety is a fluorescent amine.

8. The compound of claim 1, wherein the fluorescent moiety is 5-(dimemethylamino)naphthalene-sulfonyl (dansyl), 1-(Bromoacetyl)pyrene, 3Bromoacetyl-7-diethylaminocoumarin, 3-Bromomethyl-6,7-dimethoxycoumarin, 8-Bromomethyl-4,4-difluoro-1,3,5,7-tetramethyl-4-bora-3a, 4a-diaza-s-indacene, 3-Bromomethyl-6,7-dimethoxy-1-methyl-2 (1H)-quinoxazolinone, 6-Bromoacetyl-2-dimethylaminonaphthalene, or 4-(9-Anthroyloxy) phenacyl bromide.

9. The compound of claim 1, wherein the radioactive moiety is $^{11}C$, $^{13}N$, $^{15}O$, $^3H$ or 18F.

10. The compound of claim 6, wherein the photoactivatable moiety is benzophenone, trifluoromethyldiazirine or tetrafluorophenyl.

11. The compound of claim 8, wherein the fluorescent moiety is 5-(dimethylamino)naphthalene-sulfonyl.

12. The compound of claim 9, wherein the radioactive moiety is $^{18}F$, $^{11}C$ or $^3H$.

13. The compound of claim 1 having the structure:

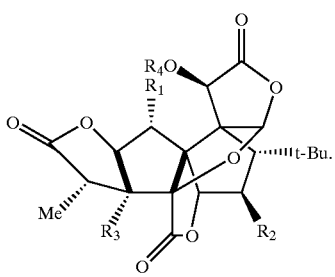

14. The compound of claim 13, wherein $R_1$ is —O-5-(dimemethylamino)naphthalene-sulfonyl.

15. The compound of claim 13, wherein $R_2$ is —O-5-(dimemethylamino)naphthalene-sulfonyl.

16. The compound of claim 13, wherein $R_2$ is —$^{11}CH_3$.

17. The compound of claim 13, wherein $R_2$ is —$CH_2CH_2{}^{18}F$.

18. The compound of claim 1, wherein $R_2$ is $^{18}F$.

19. The compound of claim 13, wherein $R_2$ is $^3H$.

20. The compound of claim 13, wherein $R_4$ is a benzophenone moiety.

21. The compound of claim 13, wherein $R_4$ is a trifluoromethyldiazirine moiety.

22. The compound of claim 13, wherein $R_4$ is a tetrafluorophenyl azide moiety.

23. The compound of claim 13, wherein $R_4$ is —$^{11}CH_3$.

24. The compound of claim 13, wherein $R_4$ is —$CH_2CH_2{}^{18}F$.

25. The compound of claim 14, having the structure:

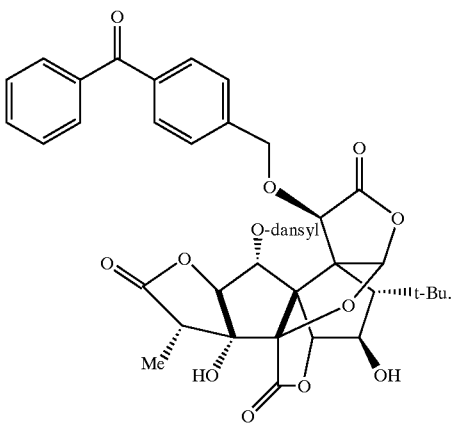

26. The compound of claim 15 having the structure:

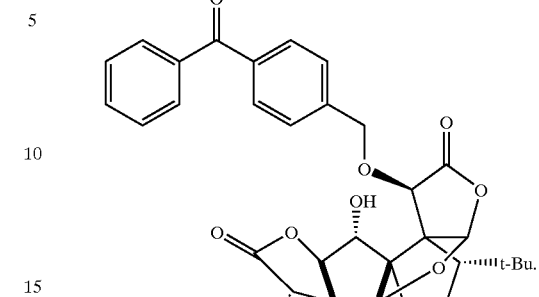

27. The compound of claim 18 having the structure:

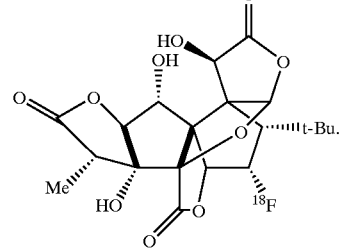

28. The compound of claim 19 having the structure:

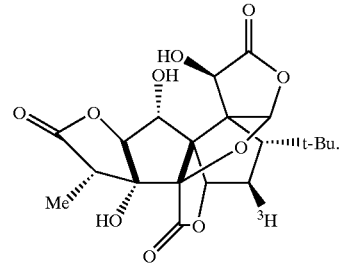

29. The compound of claim 23 having the structure:

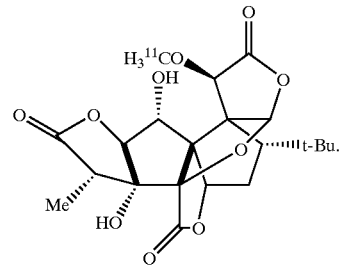

30. The compound of claim 24 having the structure:

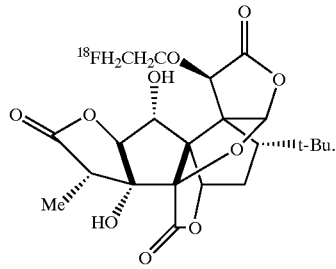

31. The compound of claim 13 having the structure:

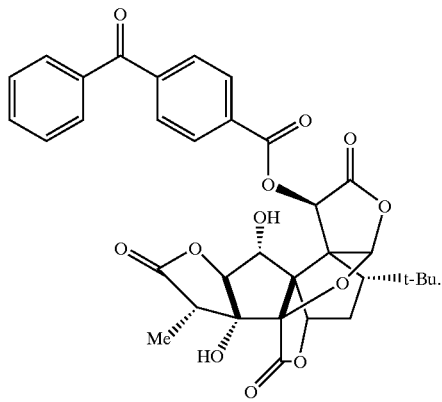

32. The compound of claim 20 having the structure:

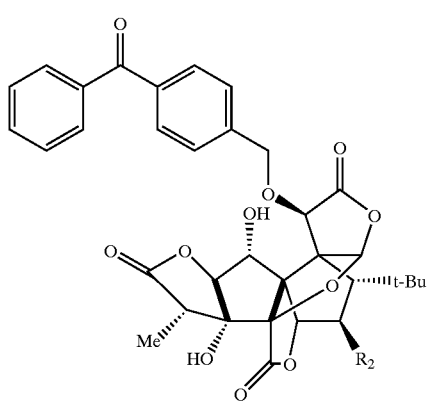

wherein $R_2$ is H or OH.

33. The compound of claim 21 having the structure:

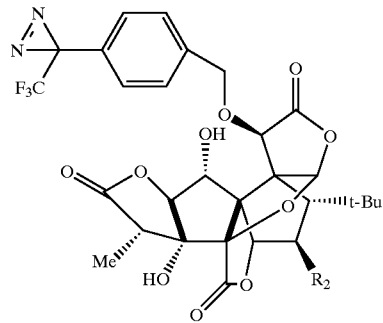

wherein $R_2$ is H or OH.

34. The compound of claim 22 having the structure:

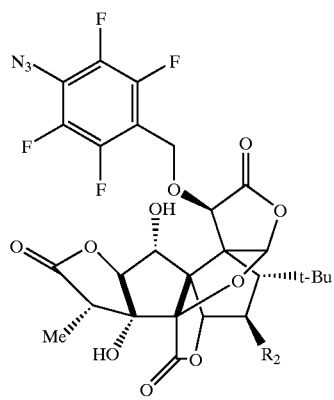

wherein $R_2$ is H or OH.

35. A compound having the structure:

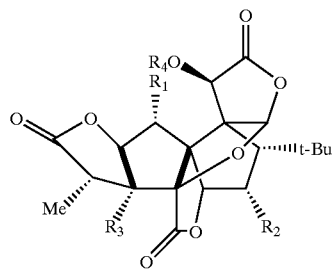

wherein $R_1$ is H, or OH;

wherein $R_2$ is OH, F, Br, unsubstituted or substituted, straight or branched alkyl group having 1 to 5 carbon atoms, an alkenyl group having 1 to 5 carbon atoms, or a alkynyl group having 1 to 5 carbon atoms;

wherein $R_3$ is H or OH; and wherein R₄ is H, OH, —A—Ar, —A—Z—Ar, —SO₂—Ar, or —A—NR₅, or —R₆, where A is an alkylene group having 1 to 8 carbon atoms, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —COR₅, —COR₆, —CONR₅R₆, —CO₂R₅, —NHCOR₅, —NH(OH), —N(OH)COR₅, —CHOR₅, —OCH₂CO₂R₅, —CH₂SR₅, —CH₂NR₅R₆, —SR₅, —OSR₅, —O₂NR₅R₆, —NR₅R₆, —NR₅SO₂R₆, in which R₅ and R₆ are the same or different and each is hydrogen, an alkyl group having 1 to 10 carbon atoms or a cycloalkyl group having 3 to 10 carbon atoms, —SCX₃ in which X is a halogen, —CN, —NO₂ or —Z—A—Z'— in which Z and A are as defined above and Z' represents carbon, oxygen, sulfur, or nitrogen, or an optically pure enantiomer, or a salt of the compound.

36. The compound of claim 35, wherein R₂ is F.

37. A compound having the structure:

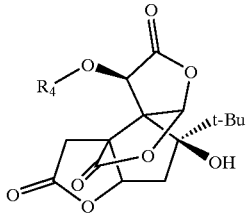

wherein R₄ is a photoactivatable moiety, a fluorescent moiety, or a radioactive moiety.

38. A compound having the structure:

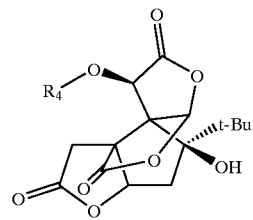

wherein R₄ is H, OH, —A—Ar, —A—Z—Ar, —SO₂—Ar, or —A—NR₅, or —R₆, where A is an alkylene group having 1 to 8 carbon atoms, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —COR₅, —COR₆, —CONR₅R₆, —CO₂R₅, —NHCOR₅, —NH(OH), —N(OH)COR₅, —CHOR₅, —OCH₂CO₂R₅, —CH₂SR₅, —CH₂NR₅R₆, —SR₅, —OSR₅, —O₂NR₅R₆, —NR₅R₆, —NR₅SO₂R₆, in which R₅ and R₆ are the same or different and each is hydrogen, an alkyl group having 1 to 10 carbon atoms or a cycloalkyl group having 3 to 10 carbon atoms, —SCX₃ in which X is a halogen, —CN, —NO₂ or —Z—A—Z'— in which Z and A are as defined above and Z' represents carbon, oxygen, sulfur, or nitrogen, or an optically pure enantiomer, or a salt of the compound.

39. A process for detecting the binding of the compound of claim 1 to a target, comprising contacting the compound with the target and detecting the binding of the compound to the target.

* * * * *